United States Patent [19]
Daugan et al.

[11] Patent Number: 6,001,847
[45] Date of Patent: Dec. 14, 1999

[54] CHEMICAL COMPOUNDS

[75] Inventors: Alain Claude-Marie Daugan, Les Ulis, France; Richard Frederic LaBaudiniere, Collegeville, Pa.

[73] Assignee: ICOS Corporation, Bothell, Wash.

[21] Appl. No.: 08/981,966

[22] PCT Filed: Jul. 11, 1996

[86] PCT No.: PCT/EP96/03023

§ 371 Date: Jun. 8, 1998

§ 102(e) Date: Jun. 8, 1998

[87] PCT Pub. No.: WO96/32003

PCT Pub. Date: Oct. 17, 1996

[30] Foreign Application Priority Data

Jul. 14, 1995 [GB] United Kingdom .................. 9414473

[51] Int. Cl.$^6$ .......................... A01N 43/42; A01N 43/58; C07D 239/00; C07D 471/00

[52] U.S. Cl. .......................... 514/287; 544/247; 544/343; 546/64; 546/85; 546/86; 546/87; 514/92; 514/249; 514/250

[58] Field of Search .................................. 544/247, 343; 546/64, 85, 86, 87; 514/92, 287, 249, 250

[56] References Cited

U.S. PATENT DOCUMENTS

| | | | |
|---|---|---|---|
| 3,644,384 | 2/1972 | Schulenberg | 260/295 C |
| 3,717,638 | 2/1973 | Schulenberg | 260/268 PC |
| 3,917,599 | 11/1975 | Saxena et al. | 544/343 |
| 4,188,390 | 2/1980 | Campbell | 424/251 |
| 4,686,228 | 8/1987 | Campbell et al. | 514/307 |
| 5,145,852 | 9/1992 | Virag | 514/253 |
| 5,270,323 | 12/1993 | Milne, Jr. et al. | 514/309 |

FOREIGN PATENT DOCUMENTS

| | | | |
|---|---|---|---|
| 0 357 122 | 3/1990 | European Pat. Off. | C07D 471/04 |
| 0 362 555 | 4/1990 | European Pat. Off. | C07D 241/08 |
| 459 666 | 12/1991 | European Pat. Off. | A61K 31/505 |
| 463 756 | 1/1992 | European Pat. Off. | C07D 487/04 |
| 526 004 | 2/1993 | European Pat. Off. | C07D 487/04 |
| 03044324 | 2/1991 | Japan | A61K 31/52 |
| 1 454 171 | 10/1975 | United Kingdom | C07D 471/14 |
| 1 454 171 | 10/1976 | United Kingdom | C07D 471/14 |
| WO 89/10123 | 11/1989 | WIPO | A61K 31/35 |
| WO 94/28902 | 12/1994 | WIPO | A61K 31/505 |
| WO 95/19978 | 7/1995 | WIPO | C07D 471/14 |

OTHER PUBLICATIONS

A. Bowman et al., *Br. J. Pharmac.*, (1984), 81, 665–674.
F. Trigo–Rocha et al., *Am. J. Physiol.*, (1993, Feb.), 264, H419–H422.
J. Reiser et al., *Br. J. Dis. Chest*, (1986), 80, 157–163.
P. Bush et al., *J. Urol.*, (1992, Jun.), 147, 1650–1655.
F. Holmquist et al., *J. Urol.* (1993, Oct.), 150, 1310–1315.
R. Rudd et al., *Br. J. Dis. Chest*, (1983), 77, 78–86.
E. McMahon et al., *J. Pharmacol. Exp. Thera.*, (1989), 251, 1000–1005.
F. Holmquist et al., *Acta Physiol. Scand.*, (1991), 143, 299–304.
G. Barbanti, *Urol. Res.*, (1988), 16, 299–302.
L. Ignarro et al., *Biochem. and Biophys. Res. Comm.*, (1990), 170(2), 843–850.
J. Krall et al., *Bio. Reprod.*, (1988), 39, 913–922.
M. Wilkins et al., *Proc. Natl. Acad. Sci., USA*, (1990, Aug.), 87, 6465–6469.
M. Wilkins et al., *J. Clin. Invest.*, (1990, Apr.), 85, 1274–1279.
J. Rajfer, *N. Eng. J. Med.*, (1992, Jan.), 326(2), 90–94.
H. Knispel, *Urol. Res.*, (1992), 20, 253–257.
G. Gwinup, *Annals. of Internal Medicine*, (1988, Jul.), 162–163.
A. Zorgniotti, *J. Urol.*, (1992, Apr.), 147(4), 308A.
K. Azadzoi et al., *J. Urol.*, (1992, Nov.), 148, 1587–1591.
K. Azadzoi et al., *J. Urol.*, (1992, Jan.), 147, 220–225.
C. Sparwasser et al., *J. Urol.*, (1994, Dec.), 152, 2159–2163.
T. Lue, "Campbell's Urology," 6th Ed., Chap. 16, P. Walsh et al., Eds., W.B. Saunders Co., 709–728 (1991).
N. Kim et al., *J. Clin. Invest.*, (1991), 88, 112–118.
S. Francis et al., in J. Beavo et al. eds. "Cyclic Nucleotide PDEs," Ch. 5 (1990) 117–140.
R. Weishaar et al., *J. Med. Chem.*, (1985), 28:5, 537–542.
H. Ahn et al., *Biochem. Pharmacol.*, (1989), 39:19, 3331–3339.
C. Lugnier et al., *Biochem. Pharamcol.*, (1986), 35:10, 1743–1751.
J. Doremieux et al., *Ann. Urol. Paris*, (1987), 21(6), 429–434.
D. Green et al., *Geriatrics*, (1993, Jan.), 48(1), 46–58.
M. Webster et al., *Hematol. Oncol. Cl. of N. Am.*, (1990, Feb.), 4(1), 265–289.
F. Holmquist et al., *Acta. Physiol. Scand.*, (1991), 141, 441–442.
J. Taher et al., *J. Urol.*, (1993, Apr.), 149, 285A.
S. Uckert et al., , 495A.
W. Aronson et al., *J. Urol.*, (1991), 145 (4 Supp.), 341A.
P. Bush et al., *Fed. Am. Soc. Exp. Biol.*, (1991), 5(4), 175.
P. Bush et al., *Fed. Am. Soc. Exp. Biol.*, (1992), 6(4), 2092.

(List continued on next page.)

*Primary Examiner*—John Kight
*Assistant Examiner*—Rita Desai
*Attorney, Agent, or Firm*—Marshall, O'Toole, Gerstein, Murray & Borun

[57] ABSTRACT

A compound of formula

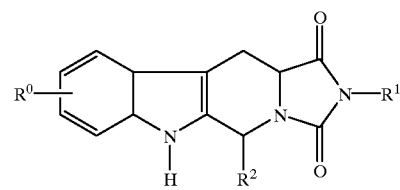

and salts and solvates thereof, wherein $R^0$, $R^1$, and $R^2$ are defined in the specification. A compound of the present invention is a potent and selective inhibitor of cGMP-specific PDE and has utility in a variety of therapeutic areas where such inhibition is beneficial.

15 Claims, No Drawings

OTHER PUBLICATIONS

W. Aronson et al., *J. Urol.*, (1992), 147 (4 Supp.), 454A.
P. Bush et al., *Circulation*, (1993, May), 87 Supp. V, V-30–V-32.
R. Pickard et al., *J. Urol.*, (1993, May) 149 (4 Supp.), 245A.
R. Pickard et al., *Clin. Pharamcol.*, (1993, Jan.), 35(5), 536P–537P.
F. Trigo–Rocha et al., *J. Urol.*, (1993, Apr.), 149, 872–877.
M. Krupp et al., *J. Cardiovas. Pharmacol.*, (1989), 13 (Supp. 2), S11–S19.
"Physicians' Desk Reference," (1992), 683,1099–1100, 1344, 1941–1943.
R. Morales et al., *World J. Urol.*, (1990), 8, 80–83.
J. Cortijo, *Br. J. Pharmacol.*, (1993, Feb.), 108(2), 562–568.
E. Kim et al., *J. Urol.*, (1995), 153, 361–365.
S. Korenman et al., *JAGS*, (1993, Apr.), 41(4), 363–366.
K. Allenby et al., *Angiology*, (1991), 42, 418–420.
H. Hamilton et al., *J. Med. Chem.*, (1987), 30, 91–96.
H. Padma–Nathan et al., *Sem. in Urol.*, (1986, Nov.), vol. IV, No.4, 236–238.
J. Beavo et al., *TiPS*, (1990, Apr.), 11, 150–155.
S. Korenman et al., *Clin. Res.*, (1988), 36, 123A.
D. Halsted et al., *J. Urol.*, (1986, Jul.), 136, 109–110.
W. Thompson, *Pharmac. Ther.*, (1991), 51, 13–33.
M. Geimbycz et al., *Clin. and Exper. Allergy*, (1992), 22, 337–344.
C. Nicholson et al., *TIPS*, (1991, Jan.), 12, 19–27.
J. LeBlanc et al., *Eur. J. Cardiothorac Surg.*, (1993), 7, 211–215.
C. Stief et al., *J. Urol.*, (1992, Nov.), 148, 1437–1440.
C. Stief et al., *World J. Urol.*, (1991), 9, 237–239.
C. Clyne et al., *Br. J. Surg.*, (1987, Apr.), 74, 246–248.
V. Mirone et al., *Acta. Urol. Ltd.*, (1992), Suppl. 4, 11–12.
P. Bush, Ph.D. Thesis (1992), pp. 159–160.
T. Lincoln, *Pharmac. Ther.*, (1989), 41, 479–502.
J. Heaton et al., *Urology*, (Feb. 1995), 45(2), 200–206.
Maria Lopez–Rodriguez et al, Steorospecificity . . . , J of Org. Chem. vol. 59, 1994 pp. 1583–1585, Oct. 1993.
E.G. Mc.Mohon et al., Depressor . . . , J of Pharm and Expt. Therapeutics . . . vol. 251 No. 3, Aug. 1989.
G. Barbanti,P. Beneforti et al, Urological Research, 1988 pp. 299–302, Dec. 1987.
Beyer et al., *Phys. and Behav.*, (1981), 27, 731–733.
Pickard et al., *Br. J. Pharamcol.*, (1991), 104 755–759.
Martinez–Pineiro et al., *Eur. Urol.*, (1993), 24, 492–499.
Mirone et al., *Br. J. Urol.*, (Mar., 1993), 71(3), 365.
Murray et al., *Biochemical Soc. Trans.*, (1992), 20, 460–464.
Raeburn et al., *Prog. Drug Res.*, (1993), 12–32.
Merkel, *Cardio. Drug. Rev.*, (1993), 11(4), 501–515.
"Physicians' Desk Reference," (1992) 2207–2208.
Cimino et al., *Biochem. Pharmacology*, (1988), 37(14), 2739–2745.
Watanabe et al., *Federation Proceedings*, (1982), 41(7), 2292–2399.
Earl et al., *Life Sciences*, (1984), 35, 525–534.
Brindley, *Brit. J. Phychiat.*, (1983), 143, 332–337.
Keogh, *Aust. NZ. J. Med.*, (1989), 19, 108–112.
Funderbunk, *New Engl. J. Med.*, (1974), 290, 630–631.
Beretta, *Acta European Fertilitatis*, (1986), 17, 43–45.
"Physicians' Desk Reference," (1992), 1778–1779.
Hess in "Prazosin: Evaluation of a New Antihypertensive Agent," D. Cotton ed., American Elsevier, NY, (1974), 3–15.
Dadkar et al., *Ind. J. Exp. Biol.*, (1982), 20, 484–487.
D'Armiento et al., *Eur. J. Pharmacol.*, (1980), 65, 234–247.
Bhalla et al., *Brit. Med. J.*, (1979), 2, 1059.
Burke et al., *Med. J. Aust.*, (1980), 382–383.
Segasouthy et al., *Med. J. Malaysia*, (1982), 37(4), 384.
Ylitalo et al., *Acta Med. Scand.*, (1983), 213, 319–320.
Robbins et al., *J. Urol.*, (1983), 130, 975.
Adams et al., *J. Urol.*, (1984), 132, 1208.
Russell et al., *Med. J. Aust.*, (1985), 143, 321.
Taher et al., *Int. J. Impotence Res.*, Abstracts, Milan, Italy (Sep. 14–17, 1992).
Lopez–Rodriguez et al., *Chemical and Pharmaceutical Bulletin*, vol. 43, No. 6, (Jun., 1995), pp. 941–946.
Miguel et al., *Journal of Heterocyclic Chemistry*, vol. 31, No. 5 (1994) pp. 1235–1239.
Lopez–Rodriguez et al., *Journal of Organic Chemistry*, vol. 59, No. 6 (1994) pp. 1583–1595.
Brana et al., *Journal of Heterocyclic Chemistry*, vol. 27, No. 3 (1990), pp. 703–706.
Brana et al., *Synthetic Communications*, vol. 20, No. 12, (1990) pp. 1793–1810.
Sandrin et al., *Heterocycles*, vol. 4, No. 7 (1976) pp. 1249–1255.
Brana et al., *Liebigs Annalen der Chemie*, No. 8 (1992) pp. 867–869.
Saxena et al., *Journal of Medicinal Chemistry*, vol. 16, No. 5, 560–564 (1973).
Ishida et al., *Chem. Pharm. Bull.*, vol. 33, No. 8, 3237–3249 (1985).
Gillespie et al., *Molecular Pharmacology*, 36:773–781 (1989).
Braña et al., *Synthetic Communications*, 20(12), 1793–1820 (1990).
Dellouve–Courillon et al., *Tetrahedron*, 46, No. 9, 3245–3266 (1990).
Murray, *DN&P* 6(3), 150–156 (1993).
Zorgniotti et al. *Int. J. Impotence Res.*, 6, 33–36 (1994).

CHEMICAL COMPOUNDS

This application is a priority 371 of PCT/EP96/03023 filed Jul. 11, 1997.

This invention relates to a series of tetracyclic derivatives, to processes for their preparation, pharmaceutical compositions containing them, and their use as therapeutic agents. In particular, the invention relates to tetracyclic derivatives which are potent and selective inhibitors of cyclic guanosine 3', 5'-monophosphate specific phosphodiesterase (cGMP specific PDE) having utility in a variety of therapeutic areas where such inhibition is thought to be beneficial, including the treatment of cardiovascular disorders.

Thus, according to a first aspect, the present invention provides compounds of formula (I)

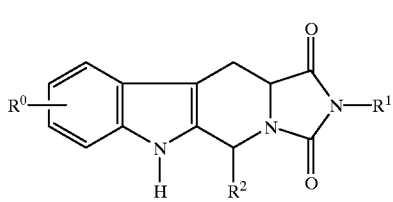

(I)

and salts and solvates (e.g. hydrates) thereof, in which:
$R^0$ represents hydrogen, halogen or $C_{1-6}$ alkyl;
$R^1$ is selected from the group consisting of:
  (a) hydrogen;
  (b) $C_{1-6}$alkyl optionally substituted by one or more substituents selected from phenyl, halogen, —$CO_2R^a$ and —$NR^aR^b$;
  (c) $C^{3-6}$cycloalkyl;
  (d) phenyl; and
  (e) a 5- or 6-membered heterocyclic ring containing at least one heteroatom selected from oxygen, nitrogen and sulphur, and being optionally substituted by one or more $C_{1-6}$alkyl, and optionally linked to the nitrogen atom to which $R^1$ is attached via $C_{1-6}$alkyl;
R is selected from the group consisting of:
  (f) $C_{3-6}$cycloalkyl;
  (g) phenyl optionally substituted by one or more substituents selected from —$OR^a$, —$NR^aR^b$, halogen, hydroxy, trifluoromethyl, cyano and nitro;
  (h) a 5- or 6-membered heterocyclic ring containing at least one heteroatom selected from oxygen, nitrogen and sulphur; and

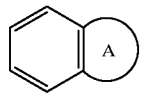

(i) a bicyclic ring attached to the rest of the molecule via one of the benzene ring carbon atoms and A is a 5- or 6-membered heterocyclic ring as defined in point (h); and $R^a$ and $R^b$ independently represent hydrogen or $C_{1-6}$alkyl.

The term "$C_{1-6}$alkyl" as used herein denotes any straight or branched alkyl chain containing 1 to 6 carbon atoms, and includes methyl, ethyl, n-propyl, iso-propyl, n-butyl, pentyl, hexyl and the like.

The term "halogen" as used herein denotes fluorine, chlorine, bromine and iodine.

A particular group of compounds according to formula (I) are those wherein $R^0$ represents any of hydrogen, methyl, bromine and fluorine, although of course the definition of $R^0$ given in formula (I) includes within its scope other $C_{1-6}$alkyl and halogen groups.

Aptly, $R^1$ may represent a substituent selected from methyl, ethyl optionally substituted by one or more chlorine atoms, butyl, cyclohexyl and benzyl.

Other suitable $R^1$ substituents include hydrogen; cycloalkyl groups, such as cyclopropyl; $C_{1-6}$alkyl, typically ethyl or propyl, substituted by an —$NR^aR^b$ substituent, such as a dimethylamino substituent; phenyl optionally linked to the nitrogen atom to which $R^1$ is attached via a $C_{1-6}$alkyl chain, such as ethyl or the like; and $C_{1-6}$alkyl, e.g. methyl, substituted by —$CO_2R^a$, such as —$CH_2CO_2Et$ or the like.

Suitable heterocyclic rings within the definition of $R^1$ include pyridyl, morpholinyl, piperazinyl, pyrrolidinyl and piperidinyl. Generally such heterocyclic rings are linked to the nitrogen atom to which $R^1$ is attached via a $C_{1-6}$alkyl chain, more appropriately a $C_{1-4}$alkyl chain.

A particularly apt substituent represented by $R^2$ is

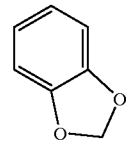

Other suitable $R^2$ substituents include thienyl, pyridyl, furyl and phenyl, wherein phenyl can be substituted by one or more substituents selected from —$OR^a$ (e.g. methoxy), —$NR^aR^b$ (e.g. dimethylamino), halogen (in particular chlorine or fluorine), hydroxy, trifluoromethyl, cyano and nitro.

Alternatively, $R^2$ may represent a suitable $C_{3-6}$cycloalkyl group, such as cyclohexyl or the like.

The pharmaceutically acceptable salts of the compounds of formula (I) which contain a basic centre are acid addition salts formed with pharmaceutically acceptable acids. Examples include the hydrochloride, hydrobromide, sulphate or bisulphate, phosphate or hydrogen phosphate, acetate, benzoate, succinate, fumarate, maleate, lactate, citrate, tartrate, gluconate, methanesulphonate, benzenesulphonate and p-toluenesulphonate salts. Compounds of the formula (I) can also provide pharmaceutically acceptable metal salts, in particular alkali metal salts, with bases. Examples include the sodium and potassium salts.

It is to be understood that the present invention covers all appropriate combinations of particular and preferred groupings hereinabove.

Particular individual compounds of the invention include:
  Cis-2-benzyl-5-(3,4-methylenedioxyphenyl)-5,6, 11,11a-tetrahydro-1H-imidazo [1', 5':1,6]pyrido[3,4-b]indole-1,3(2H)-dione;
  Trans-2-benzyl-5-(3,4-methylenedioxyphenyl)-5,6, 11,11a-tetrahydro-1H-imidazo [1', 5':1,6]pyrido[3,4-b]indole-1,3(2H)-dione;
  Cis-5-(4-methoxyphenyl)-2-methyl-5,6,11,11a-tetrahydro-1H-imidazo [1', 5':1,6]pyrido[3,4-b]indole-1,3(2H)-dione;
  Cis-2-ethyl-5-(4-methoxyphenyl)-5,6,11,11a-tetrahydro-1H-imidazo[1', 5':1,6]pyrido[3,4-b]indole-1,3(2H)-dione;
  Trans-2-ethyl-5-(4-methoxyphenyl)-5,6,11,11a-tetrahydro-1H-imidazo[1', 5':1,6]pyrido[3,4-b]indole-1,3(2H)-dione;

Trans-2-ethyl-5-(3,4-methylenedioxyphenyl)-5,6,11,11a-tetrahydro-1H-imidazo [1', 5':1,6]pyrido[3,4-b]indole-1,3(2H)-dione;

Trans-2-ethyl-5-(2-thienyl)-5,6,11,11a-tetrahydro-1H-imidazo[1', 5':1,6]pyrido [3,4-b]indole-1,3(2H)-dione;

Trans-5-(4-dimethylaminophenyl)-2-ethyl-5,6,11,11a-tetrahydro-1H-imidazo [1', 5':1,6] pyrido[3,4-b]indole-1,3(2H)-dione;

Trans-2-butyl-9-methyl-5-phenyl-5,6,11,11a-tetrahydro-1H-imidazo[1', 5':1,6]pyrido[3,4-b]indole-1,3(2H)-dione;

Trans-9-bromo-2-butyl-5-phenyl-5,6,11,11a-tetrahydro-1H-imidazo[1', 5':1,6]pyrido[3,4-b]indole-1,3(2H)-dione;

Cis-2-butyl-5-(4-methoxyphenyl)-5,6,11,11a-tetrahydro-1H-imidazo [1',5':1,6]pyrido[3,4-b]indole-1,3(2H)-dione;

Trans-2-butyl-5-(4-methoxyphenyl)-5,6,11,11a-tetrahydro-1H-imidazo [1', 5':1,6]pyrido[3,4-b]indole-1,3(2H)-dione;

Cis-2-butyl-9-fluoro-5-(4-methoxyphenyl)-5,6,11,11a-tetrahydro-1H-imidazo [1', 5':1,6]pyrido[3,4-b]indole-1,3(2H)-dione;

Trans-2-butyl-9-fluoro-5-(4-methoxyphenyl)-5,6,11,11a-tetrahydro-1H-imidazo [1',5':1,6] pyrido[3,4-b]indole-1,3(2H)-dione;

Trans-2-butyl-5-(3,4-methylenedioxyphenyl)-5,6,11,11a-tetrahydro-1H-imidazo [1',5':1,6] pyrido[3,4-b]indole-1,3(2H)-dione;

Cis-2-butyl-5-(3-chlorophenyl)-5,6,11,11a-tetrahydro-1H-imidazo[1',5':1,6]pyrido [3,4-b]indole-1,3(2H)-dione;

Trans-2-butyl-5-(3-chlorophenyl)-5,6,11,11a-tetrahydro-1H-imidazo[1',5':1,6]pyrido [3,4-b]indole-1,3(2H)-dione;

Cis-2-butyl-5-(4-chlorophenyl)-5,6,11,11a-tetrahydro-1H-imidazo [1', 5':1,6]pyrido [3,4-b]indole-1,3(2H)-dione;

Trans-2-butyl-5-(4-chlorophenyl)-5,6,11,11a-tetrahydro-1H-imidazo [1',5':1,6]pyrido[3,4-b]indole1,3(2H)-dione;

Trans-2-butyl-5-(4-fluorophenyl)-5,6,11,11a-tetrahydro-1H-imidazo[1',5':1,6]pyrido [3,4-b]indole-1,3(2H)-dione;

Trans-2-butyl-5-(4-hydroxyphenyl)-5,6,11,11a-tetrahydro-1H-imidazo[1', 5':1,6]pyrido [3,4-b]indole-1,3(2H)-dione;

Cis-2-butyl-5-(4-trifluoromethylphenyl)-5,6,11,11a-tetrahydro-1H-imidazo [1',5':1,6]pyrido[3,4-b]indole-1,3(2H)-dione;

Cis-2-butyl-5-(4-cyanophenyl)-5,6,11,11a-tetrahydro-1H-imidazo[1',5':1,6] pyrido [3,4-b]indole-1,3(2H)-dione;

Trans-2-butyl-5-(4-cyanophenyl)-5,6,11,11a-tetrahydro-1H-imidazo[1',5':1,6]pyrido[3,4-b]indole-1,3(2H)-dione;

Cis-2-butyl-5-(4-nitrophenyl)-5,6,11,11a-tetrahydro-1H-imidazo[1',5':1,6]pyrido [3,4-b]indole-1,3(2H)-dione;

Trans-2-butyl-5-(4-nitrophenyl)-5,6,11,11a-tetrahydro-1H-imidazo[1',5':1,6]pyrido[3,4-b]indole-1,3(2H)-dione;

Cis-2-butyl-5-(3-pyridyl)-5,6,11,11a-tetrahydro-1H-imidazo[1',5':1,6]pyrido [3,4-b]indole-1,3(2H)-dione;

Cis-2-butyl-5-(3-thienyl)-5,6,11,11a-tetrahydro-1H-imidazo[1',5':1,6]pyrido [3,4-b]indole-1,3(2H)-dione;

Trans-2-butyl-5-(3-thienyl)-5,6,11,11a-tetrahydro-1H-imidazo[1', 5':1,6]pyrido[3,4-b]indole-1,3(2H)-dione;

Cis-2-butyl-5-(3-furyl)-5,6,11,11a-tetrahydro-1H-imidazo[1',5':1,6]pyrido [3,4-b]indole-1,3(2H)-dione;

Trans-2-butyl-5-(3-furyl)-5,6,11,11a-tetrahydro-1H-imidazo[1',5':1,6]pyrido[3,4-b]indole-1,3(2H)-dione;

Cis-2-cyclohexyl-5-(4-methoxyphenyl)-5,6,11,11a-tetrahydro-1H-imidazo [1',5':1,6] pyrido[3,4-b]indole-1,3(2H)-dione;

Trans-2-cyclohexyl-5-(4-methoxyphenyl)-5,6,11,11a-tetrahydro-1H-imidazo [1', 5':1,6]pyrido[3,4-b]indole-1,3(2H)-dione;

Cis-2-cyclohexyl-9-fluoro-5-(4-methoxyphenyl)-5,6,11,11a-tetrahydro-1H-imidazo [1',5':1,6]pyrido[3,4-b]indole-1,3(2H)-dione; Trans-2-cyclohexyl-9-fluoro-5-(4-methoxyphenyl)-5,6, 1 1,1 1 a-tetrahydro-1H-imidazo [1', 5':1,6] pyrido[3,4-b]indole-1,3(2H)-dione;

Trans-2-benzyl-5-phenyl-5,6,11,11a-tetrahydro-1H-imidazo[1',5':1,6]pyrido [3,4-b]indole-1,3(2H)-dione;

Cis-2-benzyl-5-(4-methoxyphenyl)-5,6,11,11a-tetrahydro-1H-imidazo[1',5':1,6]pyrido [3,4-b]indole-1,3(2H)-dione;

Trans-2-benzyl-5-(4-methoxyphenyl)-5,6,11,11a-tetrahydro-1H-imidazo[1',5':1,6]pyrido [3,4-b]indole-1,3(2H)-dione;

(5R,11aR)-2-benzyl-5-(3,4-methylenedioxyphenyl)-5,6,11,11a-tetrahydro-1H-imidazo [1',5':1,6]pyrido[3,4-b]indole-1,3(2H)-dione;

Trans-2-benzyl-5-(4-hydroxyphenyl)-5,6,11,11a-tetrahydro-1H-imidazo [1',5':1,6]pyrido [3,4-b]indole-1,3(2H)-dione;

Trans-2-(2-chloroethyl)-5-(4-methoxyphenyl)-5,6,11,11a-tetrahydro-1H-imidazo [1', 5':1,6]pyrido[3,4-b]indole-1,3(2H)-dione;

Cis-2-benzyl-5-cyclohexyl-5,6,11,11a-tetrahydro-1H-imidazo[1',5':1,6]pyrido[3,4-b]indole-1,3(2H)-dione;

Trans-2-benzyl-5-cyclohexyl-5,6,11,11a-tetrahydro-1H-imidazo[1',5':1,6]pyrido[3,4-b]indole-1,3(2H)-dione;

Trans-2-butyl-5-phenyl-5,6,11,11a-tetrahydro-1H-imidazo[1',5':1,6]pyrido[3,4-b]indole-1,3(2H)-dione;

Trans-2-cyclohexyl-5-phenyl-5,6,11,11a-tetrahydro-1H-imidazo[1',5':1,6] pyrido [3,4-b]indole-1,3(2H)-dione;

Cis-2-cyclohexyl-5-phenyl-5,6,11,11a-tetrahydro-1H-imidazo[1',5':1,6] pyrido [3,4-b]indole-1,3(2H)-dione;

Trans-2-ethoxycarbonylmethyl-5-(4-methoxyphenyl)-5,6,11,11a-tetrahydro-1H-imidazo [1', 5':1,6] pyrido [3,4-b]indole-1,3(2H)-dione;

Trans-5-(4-methoxyphenyl)-2-[2-(2-pyridyl)-ethyl]-5,6,11,11a-tetrahydro-1H-imidazo [1',5':1,6]pyrido[3,4-b]indole-1,3(2H)-dione;

Trans-2-cyclopropyl-5-phenyl-5,6,11,11a-tetrahydro-1H-imidazo[1',5':1,6]pyrido[3,4-b]indole-1,3(2H)-dione;

Trans -2-phenethyl-5-phenyl-5,6,11,11a-tetrahydro-1H-imidazo[1',5':1,6]pyrido[3,4-b]indole-1,3(2H)-dione;

Trans-5-phenyl-2-(2-pyridylmethyl)-5,6,11,11a-tetrahydro-1H-imidazo [1',5':1,6]pyrido[3,4-b]indole-1,3(2H)-dione;

Trans-5-phenyl-2-(4-pyridylmethyl)-5,6,11,11a-tetrahydro-1H-imidazo [1',5':1,6]pyrido[3,4-b]indole-1,3(2H)-dione;

Trans-5-(4-methoxyphenyl)-2-(3-pyridylmethyl)-5,6,11,11a-tetrahydro-1H-imidazo [1',5':1,6]pyrido[3,4-b]indole-1,3(2H)-dione;

Trans-2-(2-dimethylamino-ethyl)-5-(4-methoxyphenyl)-5,6,11,11a-tetrahydro-1H-imidazo [1',5':1,6]pyrido [3,4-b]indole-1,3(2H)-dione;

Trans-2-(3-dimethylamino-propyl)-5-(4-methoxyphenyl)-5,6,11,11a-tetrahydro -1H-imidazo [1', 5':1,6] pyrido [3,4-b]indole-1,3(2H)-dione;

Trans-2-(2-morpholin-4-yl-ethyl)-5-phenyl-5,6,11,11a-tetrahydro-1H-imidazo [1', 5':1,6] pyrido [3,4-b] indole-1,3(2H)-dione;

Trans-5-(4-methoxyphenyl)-2-[3-(4-methyl-piperazin-1-yl)-propyl]-5,6,11,11a-tetrahydro-1H-imidazo [1', 5':1,6] pyrido [3,4-b]indole-1,3(2H)-dione;

Trans-5-(4-methoxyphenyl)-2-(2-pyrrolidin-1-yl-ethyl)-5,6,11,11a-tetrahydro-1H-imidazo [1', 5':1,6] pyrido [3,4-b]indole-1,3(2H)-dione;

Trans-5-(4-methoxyphenyl)-2-[2-(1-methyl-pyrrolidin-2-yl)-ethyl]-5,6,11,11a-tetrahydro -1H-imidazo [1',5':1,6] pyrido [3,4-b]indole-1,3(2H)-dione;

Trans-5-(4-methoxyphenyl)-5,6,11,11a-tetrahydro-1H-imidazo[1',5':1,6] pyrido [3,4-b]indole-1,3 (2H)-dione;

Cis-5-(4-methoxyphenyl)-5,6,11,11a-tetrahydro-1H-imidazo[1',5':1,6] pyrido [3,4-b]indole-1,3 (2H)-dione;

and pharmaceutically acceptable salts and solvates thereof.

Particularly preferred compounds of the invention are:

(5R,11aR)-2-benzyl-5-(3,4-methylenedioxyphenyl)-5,6,11,11a-tetrahydro-1H-imidazo [1',5':1,6]pyrido[3,4-b]indole-1,3(2H)-dione;

Cis-2-cyclohexyl-5-(4-methoxyphenyl)-5,6,11,11a-tetrahydro-1H-imidazo [1',5':1,6] pyrido[3,4-b]indole-1,3(2H)-dione;

Trans-2-butyl-5-(4-methoxyphenyl)-5,6,11,11a-tetrahydro-1H-imidazo [1',5':1,6]pyrido[3,4-b]indole-1,3(2H)-dione;

Cis-2-benzyl-5-(3,4-methylenedioxyphenyl)-5,6,11,11a-tetrahydro-1H-imidazo [1',5':1,6]pyrido[3,4-b]indole-1,3(2H)-dione;

and pharmaceutically acceptable salts and solvates thereof.

It has been shown that compounds of the present invention are potent and selective inhibitors of cGMP specific PDE. Thus, compounds of formula (I) are of interest for use in therapy, specifically for the treatment of a variety of conditions where inhibition of cGMP specific PDE is thought to be beneficial.

As a consequence of the selective PDE V inhibition exhibited by compounds of the present invention, cGMP levels are elevated, which in turn can give rise to beneficial anti-platelet, anti-neutrophil, anti-vasospastic, vasodilatory, natriuretic and diuretic activities as well as potentiation of the effects of endothelium-derived relaxing factor (EDRF), nitrovasodilators, atrial natriuretic factor (ANF), brain natriuretic peptide (BNP), C-type natriuretic peptide (CNP) and endothelium-dependent relaxing agents such as bradykinin, acetylcholine and 5-HT$_1$. The compounds of formula (I) therefore have utility in the treatment of a number of disorders, including stable, unstable and variant (Prinzmetal) angina, hypertension, pulmonary hypertension, congestive heart failure, renal failure, atherosclerosis, conditions of reduced blood vessel patency (e.g. post-percutaneous transluminal coronary angioplasty), peripheral vascular disease, vascular disorders such as Raynaud's disease, inflammatory diseases, stroke, bronchitis, chronic asthma, allergic asthma, allergic rhinitis, glaucoma, erectile dysfunction and diseases characterised by disorders of gut motility (e.g. irritable bowel syndrome).

It will be appreciated that references herein to treatment extend to prophylaxis as well as treatment of established conditions.

It will also be appreciated that 'a compound of formula (I),' or a physiologically acceptable salt or solvate thereof can be administered as the raw compound, or as a pharmaceutical composition containing either entity.

There is thus provided as a further aspect of the invention a compound of formula (I) for use in the treatment of stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma, erectile dysfunction or diseases characterised by disorders of gut motility (e.g. IBS).

According to another aspect of the invention, there is provided the use of a compound of formula (I) for the manufacture of a medicament for the treatment of stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma, erectile dysfunction or diseases characterised by disorders of gut motility (e.g. IBS).

In a further aspect, the invention provides a method of treating stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma, erectile dysfunction or diseases characterised by disorders of gut motility (e.g. IBS) in a human or non-human animal body which comprises administering to said body a therapeutically effective amount of a compound with formula (I).

Compounds of the invention may be administered by any suitable route, for example by oral, buccal, sub-lingual, rectal, vaginal, nasal, topical or parenteral (including intravenous, intramuscular, subcutaneous and intracoronary) administration. Oral administration is generally preferred.

For administration to man in the curative or prophylactic treatment of the disorders identified above, oral dosages of a compound of formula (I) will generally be in the range of from 0.5–800 mg daily for an average adult patient (70 kg). Thus for a typical adult patient, individual tablets or capsules contain from 0.2400 mg of active compound, in a suitable pharmaceutically acceptable vehicle or carrier, for administration in single or multiple doses, once or several times per day. Dosages for intravenous, buccal or sublingual administration will typically be within the range of from 0.1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, a compound of the formula (I) can be administered alone, but will generally be administered in admixture with a pharmaceutical carrier selected with regard to the intended route of administration and standard pharmaceutical practice. For example, the compound may be administered orally, buccally or sublingually, in the form of tablets containing excipients such as starch or lactose, or in capsules or ovules either alone or in admixture with excipients, or in the form of elixirs or suspensions containing flavouring or colouring agents. Such liquid preparations may be prepared with pharmaceutically acceptable additives such as suspending agents (e.g. methylcellulose, a semi-synthetic glyceride such as witepsol or mixtures of glycerides such as a mixture of apricot kernel oil and PEG-6 esters or mixtures of PEG-8 and caprylic/capric glycerides). A compound may also be injected parenterally, for example intravenously, intramuscularly, subcutaneously or intracoronarily. For parenteral administration, the compound is best used in the form of a sterile aqueous solution which may contain other substances, for example salts, or monosaccharides such as mannitol or glucose, to make the solution isotonic with blood.

Thus, the invention provides in a further aspect a pharmaceutical composition comprising a compound of the formula (I) together with a pharmaceutically acceptable diluent or carrier therefor.

There is further provided by the present invention a process of preparing a pharmaceutical composition comprising a compound of formula (I), which process comprises mixing a compound of formula (I) together with a pharmaceutically acceptable diluent or carrier therefor.

A compound of formula (I) may also be used in combination with other therapeutic agents which may be useful in the treatment of the above-mentioned disease states. The invention thus provides, in another aspect, a combination of a compound of formula (I) together with another therapeutically active agent.

The combination referred to above may conveniently be presented for use in the form of a pharmaceutical formulation and thus pharmaceutical compositions comprising a combination as defined above together with a pharmaceutically acceptable diluent or carrier comprise a further aspect of the invention.

The individual components of such a combination may also be administered either sequentially or simultaneously in separate pharmaceutical formulations.

Appropriate doses of known therapeutic agents for use in combination with a compound of formula (I) will be readily appreciated by those skilled in the art.

Compounds of formula (I) may be prepared by any suitable method known in the art or by the following processes which form part of the present invention. In the methods below $R^0$, $R^1$ and $R^2$ are as defined in formula (I) above unless otherwise indicated.

Thus, a process (A) for preparing a compound of formula (I) comprises reacting a compound of formula (II)

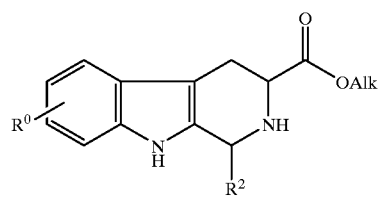

(II)

with an isocyanate of formula $R^1$—N=C=O, in the presence of a suitable organic solvent, such as a ketone solvent, e.g. butanone, acetone or the like, and under reflux for several hours, e.g. 14 to 16 hours. Alk as used herein represents a $C_{1-6}$alkyl group, e.g. methyl.

Compounds of formula (I) may be prepared as individual enantiomers in two steps from the appropriate enantiomer of formula (III) or as mixtures (e.g. racemates) of either pairs of cis or trans isomers from the corresponding mixtures of either pairs of cis or trans isomers of formula (III).

Individual enantiomers of the compounds of the invention may be prepared from racemates by resolution using methods known in the art for the separation of racemic mixtures into their constituent enantiomers, for example using HPLC (high performance liquid chromatography) on a chiral column such as Hypersil naphthylurea.

A compound of formula (II) may conveniently be prepared from a tryptophan derivative, such as an alkyl ester thereof of formula (III)

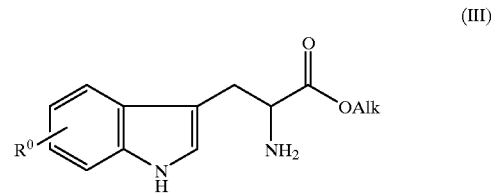

(III)

(where Alk is as previously defined) or a salt thereof (e.g. the hydrochloride salt) according to either of the following procedures (a) and (b). Procedure (b) is only suitable for preparing cis isomers of formula (III) and may be particularly suitable for preparing individual cis enantiomers of formula (III) from D- or L-tryptophan alkyl esters as appropriate.

Procedure (a)

This comprises a Pictet-Spengler cyclisation between a compound of formula (III) and an aldehyde $R^2CHO$. The reaction may conveniently be effected in a suitable solvent such as a halogenated hydrocarbon (e.g. dichloromethane) or an aromatic hydrocarbon (e.g. toluene) in the presence of an acid such as trifluoroacetic acid. The reaction may conveniently be carried out at a temperature of from −20° C. to reflux to provide a compound of formula (II) in one step. The reaction may also be carried out in a solvent such as an aromatic hydrocarbon (e.g. benzene or toluene) under reflux, optionally using a Dean-Stark apparatus to trap the water produced.

The reaction provides a mixture of cis and trans isomers which may be either individual enantiomers or racemates of pairs of cis or trans isomers depending upon whether racemic or enantiomerically pure tryptophan alkyl ester was used as the starting material. Individual cis or trans enantiomers may conveniently be separated from mixtures thereof by fractional crystallisation or by chromatography (e.g. flash column chromatography) using appropriate solvents and eluents. Similarly, pairs of cis and trans isomers may be separated by chromatography (e.g. flash column chromatography) using appropriate eluents. An optically pure trans isomer may also be converted to an optically pure cis isomer using suitable epimerisation procedures. One such procedure comprises treating the trans isomer or a mixture (e.g. 1:1 mixture) of cis and trans isomers with methanolic or aqueous hydrogen chloride at a temperature of from 0° C. to the refluxing temperature of the solution. The mixture may then be subjected to chromatography (e.g. flash column chromatography) to separate the resulting diastereoisomers, or in the procedure utilising aqueous hydrogen chloride the desired cis isomer precipitates out as the hydrochloride salt which may then be isolated by filtration.

Procedure (b)

This comprises a four-step procedure from a compound of formula (III) or a salt thereof (e.g. the hydrochloride salt). The procedure is particularly suitable for preparing a 1R, 3R isomer of formula (III) from a D-tryptophan alkyl ester of formula (IV) or a salt thereof (e.g. the hydrochloride salt). Thus, a first step (i) comprises treating a compound of formula (IV) with an acid halide $R^2COHal$ (where Hal is as previously defined) in the presence of a base, e.g. an organic base such as a trialkylamine (for example triethylamine), to provide a compound of formula (IV)

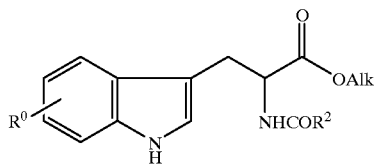
(IV)

The reaction may be conveniently carried out in a suitable solvent such as a halogenated hydrocarbon (e.g. dichloromethane) or an ether (e.g. tetrahydrofuran) and at a temperature of from −20° C. to +40° C.

Step (ii) comprises treating a compound of formula (IV) with an agent to convert the amide group to a thioamide group. Suitable sulphurating agents are well-known in the art. Thus, for example, the reaction may conveniently be effected by treating (IV) with Lawesson's reagent. This reaction may conveniently be carried out in a suitable solvent such as an ether (e.g. dimethoxyethane) or an aromatic hydrocarbon (e.g. toluene) at an elevated temperature such as from 40° C. to 80° C. to provide a compound of formula (V)

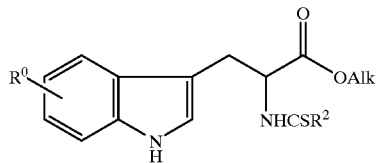
(V)

Step (iii) comprises treating a compound of formula (V) with a suitable agent to provide a compound of formula (VI)

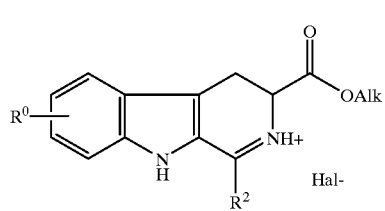
(VI)

(where Hal is a halogen atom, e.g. iodine). The reaction may conveniently be effected by treating (VI) with an alkylating agent such as a methyl halide (e.g. methyl iodide) or an acylating agent such as an acetyl halide (e.g. acetyl chloride) in a suitable solvent such as a halogenated hydrocarbon (e.g. dichloromethane) at an elevated temperature (e.g. under reflux).

In step (iv) the resulting iminium halide of formula (VI) may be treated with a reducing agent such as boron hydride, e.g. sodium borohydride, to provide the desired compound of formula (II). The reduction may conveniently be effected at a low temperature, e.g. within the range of −100° C. to 0° C., in a suitable solvent such as an alcohol (e.g. methanol).

According to a second process (B), a compound of formula (I) may be prepared by reaction of a compound of formula (VII)

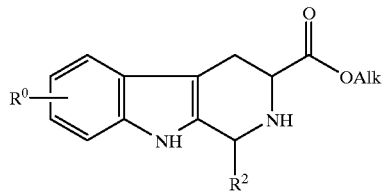
(VII)

where Alk is as previously defined, with the imidazolide of $R^1$—$NH_2$ under suitable conditions. Compounds of formula (VII) are known in the art and may be made by standard methods.

According to a third process (C), a compound of formula (I) where $R^1$ represents hydrogen may be prepared by reacting a compound of formula (VII) with urea at elevated temperature.

The pharmaceutically acceptable acid addition salts of the compounds of formula (I) which contain a basic centre may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of a compound of formula (I) with a suitable base. Both types of salt may be formed or interconverted using ion-exchange resin techniques.

Compounds of the invention may be isolated in association with solvent molecules by crystallisation from or evaporation of an appropriate solvent.

Thus, according to a further aspect of the invention, we provide a process (D) for preparing a compound of formula (I) or a salt or solvate (e.g. hydrate) thereof which comprises process (A) as hereinbefore described followed by i) an interconversion step; and/or either ii) salt formation; or iii) solvate (e.g. hydrate) formation.

The synthesis of the compounds of the invention and of the intermediates for use therein are illustrated by the following, non-limiting Examples.

INTERMEDIATES 1 and 2

Methyl 1,2,3,4-tetrahydro-1-(3,4-methylenedioxyphenyl)-9H-pyrido[3,4-b]indole-3-carboxylate, cis and trans isomers To a stirred solution of racemic tryptophan methyl ester (13 g) and piperonal (9.7 g) in anhydrous $CH_2Cl_2$ (300 mL) cooled at 0° C. was added dropwise trifluoroacetic acid (9 mL) and the solution was allowed to react at ambient temperature. After 4 days, the yellow solution was diluted with $CH_2Cl_2$ (100 mL), washed with a saturated aqueous solution of $NaHCO_3$, then with water and dried over $Na_2SO_4$. The organic layer was evaporated to dryness under reduced pressure and the residue was purified by flash chromatography eluting with $CH_2Cl_2$/MeOH (99/1) to give first Intermediate 1, the cis isomer (6.5 g) m.p. :90–93° C. followed by Intermediate 2, the trans isomer (6.4 g) m.p.:170° C.

11

The following compounds were obtained in a similar manner:

INTERMEDIATES 3 and 4

Methyl 1,2,3,4-tetrahydro-1-(4-methoxyphenyl)-9H-pyrido[3,4-b]indole-3-carboxylate, cis and trans isomers The same method as employed in the preparation of Intermediates 1 and 2 but starting from racemic tryptophan methyl ester and 4-methoxybenzaldehyde gave Intermediate 3, the cis isomer as white crystals m.p.:142° C. and Intermediate 4, the trans isomer as white crystals m.p.:209–210° C.

INTERMEDIATES 5 and 6

Methyl 1,2,3,4-tetrahydro-1-(2-thienyl)-9H-pyrido[3,4-b]indole-3-carboxylate, cis and trans isomers The same method as employed in the preparation of Intermediates 1 and 2 but starting from racemic tryptophan methyl ester and 2-thiophenecarboxaldehyde gave Intermediate 5, the cis isomer as a pale yellow solid m.p.:134–137° C. and Intermediate 6, the trans isomer as white crystals m.p.:169° C.

INTERMEDIATE 7

Ethyl 1,2,3,4-tetrahydro-1-(4-dimethylaminophenyl)-9H-pyrido[3,4-b]indole-3-carboxylate, mixture of cis and trans isomers The same method as employed in the preparation of Intermediates 1 and 2 but starting from racemic tryptophan ethyl ester and 4-dimethylaminobenzaldehyde gave the title compound as white crystals m.p.:170° C.

INTERMEDIATES 8 and 9

Methyl 1,2,3,4-tetrahydro4-fluoro-1-(4-methoxyphenyl)-9H-pyrido[3,4-b]indole-3-carboxylate, cis and trans isomers The same method as employed in the preparation of Intermediates 1 and 2 but starting from racemic 5-fluoro-tryptophan methyl ester and 4-methoxybenzaldehyde gave Intermediate 8, the cis isomer as a solid 1H NMR (CDCl$_3$) δ(ppm):7.4-6.8(m, 8 H);5.15(brs, 1 H);3.9(dd, 1 H)3.8(s, 3 H);3.2-2.9(m, 2 H) and Intermediate 9, the trans isomer as a solid m.p.:197° C.

INTERMEDIATES 10 and 11

Methyl 1,2,3,4-tetrahydro-1-(4-chlorophenyl)-9H-pyrido[3,4-b]indole-3-carboxylate, cis and trans isomers The same method as employed in the preparation of Intermediates 1 and 2 but starting from racemic tryptophan methyl ester and 4-chlorobenzaldehyde gave Intermediate 10, the cis isomer as white crystals m.p.:208–209° C. and Intermediate 11, the trans isomer as white crystals m.p.:108–109° C.

INTERMEDIATES 12 and 13

Methyl 1,2,3,4-tetrahydro-1-(4-trifluoromethylphenyl)-9H-pyrido[3,4-b]indole-3-carboxylate, cis and trans isomers The same method but starting from racemic tryptophan methyl ester and 4-trifluoromethylbenzaldehyde gave Intermediate 12, the cis isomer as pale yellow crystals m.p.:190° C. and Intermediate 13, the trans isomer as pale yellow crystals m.p.:203° C.

INTERMEDIATES 14 and 15

Ethyl 1,2,3,4-tetrahydro-1-(4-cyanophenyl)-9H-pyrido[3,4-b]indole-3-carboxylate, cis and trans isomers The same method but starting from racemic tryptophan ethyl ester and 4-cyanobenzaldehyde gave Intermediate 14, the cis isomer as white crystals m.p.:200° C. and Intermediate 15, the trans isomer as white crystals m.p.: 156° C.

INTERMEDIATES 16 and 17

Ethyl 1,2,3,4-tetrahydro-1-(4-nitrophenyl)-9H-pyrido[3,4-b]indole-3-carboxylate, cis and trans isomers The same method but starting from racemic tryptophan ethyl ester and 4-nitrobenzaldehyde gave Intermediate 16, the cis isomer as yellow crystals m.p.:168° C. and Intermediate 17, the trans isomer as yellow crystals m.p.: 195° C.

INTERMEDIATES 18 and 19

Ethyl 1,2,3,4-tetrahydro-1-(3-pyridyl)-9H-pyrido[3,4-b]indole-3-carboxylate, cis and trans isomers The same method but starting from racemic tryptophan ethyl ester and 3-pyridinecarboxaldehyde gave Intermediate 18, the cis isomer as pale yellow crystals m.p.:230–232° C. and Intermediate 19, the trans isomer as white crystals m.p.:210–214° C.

INTERMEDIATES 20 and 21

Ethyl 1,2,3,4-tetrahydro-1-(3-thienyl)-9H-pyrido[3,4-b]indole-3-carboxylate, cis and trans isomers The same method as employed in the preparation of Intermediates 1 and 2 but starting from racemic tryptophan ethyl ester and 3-thiophenecarboxaldehyde gave Intermediate 20, the cis isomer as white crystals m.p.:130° C. and Intermediate 21, the trans isomer as white crystals m.p.:182–184° C.

INTERMEDIATE 22

Methyl 1,2,3,4-tetrahydro-1-(3-furyl)-9H-pyrido[3,4-b]indole-3-carboxylate, mixture of cis and trans isomers The same method but starting from racemic tryptophan methyl ester and 3-furaldehyde gave the title compound as a yellow solid m.p.:130° C.

INTERMEDIATES 23 and 24

(1 R,3 R)-Methyl 1,2,3,4-tetrahydro-1-(3,4-methylenedioxyphenyl)-9H-pyrido[3,4-b]indole-3-carboxylate, cis isomer and (1 S,3 R)-methyl 1,2,3,4-tetrahydro-1-(3,4-methylenedioxyphenyl)-9H-pyrido[3,4-b]indole-3-carboxylate trans isomer To a stirred solution of D-tryptophan methyl ester (11 g) and piperonal (7.9 g) in anhydrous CH$_2$Cl$_2$ (400 mL) cooled at 0° C. was added dropwise trifluoroacetic acid (7.7 mL) and the solution was allowed to react at ambient temperature. After 4 days, the yellow solution was diluted with CH$_2$Cl$_2$ (200 mL) and washed with a saturated aqueous solution of NaHCO$_3$, then with water (3×200 mL) and dried over Na$_2$SO$_4$. The organic layer was evaporated under reduced pressure and the residue was purified by flash chromatography eluting with dichloromethane/ethyl acetate (97/3) to give first Intermediate 23, the cis isomer (6.5 g) m.p.:154° C. followed by Intermediate 24, the trans isomer (8.4 g) m.p.: 188° C.

INTERMEDIATE 25

Ethyl 1,2,3,4-tetrahydro-6-methyl-1-phenyl-9H-pyrido[3,4-b]indole-3-carboxylate, cis and trans isomers To a stirred mixture of racemic 5-methyl-tryptophan (4 g) in 1N H$_2$SO$_4$ (18 mL) and water (54 mL) was added benzaldehyde (2 mL) and the solution was heated at 80° C. under N$_2$ for 48 hours.The precipitated product was collected by filtration, washed with water and dried.The crude acid (4.5 g) was then dissolved in ethanol (100 mL) and the solution was cooled at −10° C.Thionyl chloride (1.2 mL) was added dropwise to the solution and the mixture was heated at 60° C. for 48 hours.The solvent was removed under reduced pressure and the residue was taken up in ice water and basified with NH$_4$OH.The precipited compound was washed with water, dried and purified by flash chromatography eluting with dichloromethane/methanol (98/2) to give first the cis isomer (1.7 g) m.p.:128–130° C., followed by the trans isomer (0.53 g) m.p.:198–200° C.

INTERMEDIATE 26

Ethyl 1,2,3,4-tetrahydro-6-bromo-1-phenyl-9H-pyrido[3,4-b]indole-3-carboxylate, cis and trans isomers The same procedure as described in the preparation of Intermediate 25 but starting from racemic 5-bromo-tryptophan and benzaldehyde gave the cis isomer as white crystals m.p.:157–160° C. and the trans isomer as white crystals m.p.:212–216° C.

INTERMEDIATE 27

Methyl 1,2,3,4-tetrahydro-1-(3-chlorophenyl)-9H-pyrido[3,4-b]indole-3-carboxylate, mixture of cis and trans isomers The same method as employed in the preparation of intermediate 1 and 2 but starting from racemic tryptophan methyl ester and 3-chlorobenzaldehyde gave the title compound as white solid m.p.:150–160° C.

INTERMEDIATE 28

Methyl 1,2,3,4-tetrahydro-1-(4-fluorophenyl)-9H-pyrido[3,4-b]indole-3-carboxylate, cis and trans isomers The same method as employed in the preparation of intermediate 1 and 2 but starting from racemic tryptophan methyl ester and 4-fluorobenzaldehyde gave the cis isomer as white crystals m.p.:92° C. and the trans isomer as pale yellow crystals m.p.:183° C.

INTERMEDIATE 29

Methyl 1,2,3,4-tetrahydro-1-(4-hydroxyphenyl)-9H-pyrido[3,4-b]indole-3-carboxylate, trans isomer To a stirred solution of racemic tryptophan methyl ester (3 g ) and 4-hydroxybenzaldehyde (1.84 g) in anhydrous dichloromethane (50 mL) cooled at 0° C. was added dropwise trifluoroacetic acid (1.27 mL) and the solution was allowed to react at ambient temperature. After 22 hours, the solution was washed with a saturated solution of NaHCO$_3$, then with water, dried over Na$_2$SO$_4$ and evaporated to dryness. The residue was purified by flash chromatography eluting with ethyl acetate to give the title compound (3.48 g) as an off-white solid m.p.:233–235° C.

EXAMPLE 1

Cis-2-benzyl-5-(3,4-methylenedioxyphenyl)-5,6,11,11a-tetrahydro-1H-imidazo [1',5':1,6]pyrido[3,4-b]indole-1,3(2H)-dione and Trans-2-benzyl-5-(3,4-methylenedioxyphenyl)-5,6,11,11a-tetrahydro-1H-imidazo [1',5':1,6]pyrido[3,4-b]indole-1,3(2H)-dione To a stirred solution of a mixture of cis and trans isomers of Intermediates 1 and 2 (1 g, 2.85 mmol) in 2-butanone (50 mL) was added dropwise benzyl isocyanate (0.37 mL, 2.99 mmol) and the mixture was refluxed for 15 hours. The solvent was then removed under reduced pressure and the residue was purified by flash chromatography eluting with toluene/ethyl acetate : 85/15 to give first, the trans isomer (240 mg) as white crystals after recrystallisation from diethyl ether. m.p.:208–210° C.

Analysis for C$_{27}$H$_{21}$N$_3$O$_4$:
Calculated: C,71.83;H,4.69;N,9.31;
Found:C,71.46;H,4.77;N,9.24%.
and followed by the cis isomer (470 mg) as white crystals after recrystallisation from ethanol. m.p.:159–161° C.

Analysis for C$_{27}$H$_{21}$N$_3$O$_4$:
Calculated: C,71.83;H,4.69;N,9.31;
Found:C,71.79;H,4.80;N,9.09%.

EXAMPLE 2

Cis-5-(4-methoxyphenyl)-2-methyl-5,6,11,11a-tetrahydro-1H-imidazo [1',5':1,6]pyrido[3,4-b]indole-1,3(2H)-dione The same method as employed in the preparation of Example 1 but starting from Intermediate 3 and methyl isocyanate gave after recrystallisation from ethanol, the title compound as white crystals m.p.:233–240° C.

Analysis for C$_{21}$H$_{19}$N$_3$O$_3$:
Calculated: C,69.79;H,5.30;N,11.63;
Found:C,69.63;H,5.29;N,11.68%.

EXAMPLE 3

Cis-2-ethyl-5-(4-methoxyphenyl)-5,6,11,11a-tetrahydro-1H-imidazo[1',5':1,6]pyrido[3,4-b]indole-1,3(2H)-dione and Trans-2ethyl-5-(4-methoxyphenyl)-5,6,11,11a-tetrahydro-1H-imidazo[1',5':1,6]pyrido[3,4-b]indole-1,3(2H)-dione The same method as employed in the preparation of Example 1 but starting from a mixture of Intermediates 3 and 4 and ethyl isocyanate gave the cis isomer as white crystals after recrystallisation from ethanol m.p.:210–220° C.

Analysis for C$_{22}$H$_{21}$N$_3$O$_3$:
Calculated: C,70.38;H,5.64;N,11.19;
Found:C,69.97;H,5.71 ;N,10.83%.

and the trans isomer as white crystals after recrystallisation from 2-propanol m.p.:245–248° C.

Analysis for $C_{22}H_{21}N_3O_3$:
Calculated: C,70.38;H,5.64;N,11.19;
Found:C,70.28;H,5.76;N,11.22%.

EXAMPLE 4

Trans-2-ethyl-5-(3,4-methylenedioxyphenyl)-5,6,11, 11a-tetrahydro-1H-imidazo [1',5':1,6]pyrido[3,4-b] indole-1,3(2H)-dione The same method as employed in the preparation of Example 1 but starting from the Intermediate 2 and ethyl isocyanate gave after recrystallisation from ethyl acetate/hexane, the title compound as white crystals m.p.:238° C.

Analysis for $C_{22}H_{19}N_3O_4$:
Calculated: C,67.86;H,4.92;N,10.79;
Found:C,68.32;H,4.90;N,10.90%.

EXAMPLE 5

Trans-2-ethyl-5-(2-thienyl)-5,6,11,11a-tetrahydro-1H-imidazo[1',5':1,6] pyrido [3,4-b]indole-1,3(2H)-dione The same method as employed in the preparation of Example 1 but starting from Intermediate 6 and ethyl isocyanate gave after recrystallisation from 2-propanol, the title compound as white crystals m.p.:242–248° C.

Analysis for $C_{19}H_{17}N_3O_2S$:
Calculated: C,64.94;H,4.88;N,11.96;
Found:C,64.79;H,5.00;N,11.88%.

EXAMPLE 6

Trans-5-(4-dimethylaminophenyl)-2-ethyl-5,6,11, 11a-tetrahydro-1H-imidazo [1',5':1.6] pyrido[3,4-b] indole-1,3(2H)-dione The same method as employed in the preparation of Example 1 but starting from a mixture of cis and trans isomers of Intermediate 7 and ethyl isocyanate gave after recrystallisation from methanol, the title compound as white crystals m.p.:262–265° C.

Analysis for $C_{23}H_{24}N_4O_2$:
Calculated: C,71.11;H,6.23;N,14.42;
Found:C,71.01;H,6.29;N,14.49%.

EXAMPLE 7

Trans-2-butyl-9-methyl-5-phenyl-5,6,11,11a-tetrahydro-1H-imidazo[1',5':1,6]pyrido[3,4-b]indole-1,3(2H)-dione The same method as employed in the preparation of Example 1 but starting from the trans isomer of Intermediate 25 and butyl isocyanate gave after recrystallisation from diisopropyl ether, the title compound as white crystals m.p. :196–198° C.

Analysis for $C_{24}H_{25}N_3O_2$:
Calculated: C,74.39;H,6.50;N,10.84;
Found:C,74.38;H,6.52;N,10.63%.

EXAMPLE 8

Trans-9-bromo-2-butyl-5-phenyl-5,6,11,11a-tetrahydro-1H-imidazo[1',5':1,6]pyrido[3,4-b]indole-1,3(2H)-dione The same method as employed in the preparation of Example 1 but starting from the trans isomer of Intermediate 26 and butyl isocyanate gave after recrystallisation from diisopropyl ether, the title compound as white crystals m.p. :207–210° C.

Analysis for $C_{23}H_{22}BrN_3O_2$:
Calculated: C,61.07;H,4.90;Br,17.66;N,9.29;
Found:C,61.28;H,4.95;Br,17.53;N,9.10%.

EXAMPLE 9

Cis-2-butyl-5-(4-methoxyphenyl)-5,6,11,11a-tetrahydro-1H-imidazo [1',5':1,6]pyrido[3,4-b] indole-1,3(2H)-dione The same method as employed in the preparation of Example 1 but starting from the Intermediate 3 and butyl isocyanate gave after recrystallisation from methanol, the title compound as white crystals m.p.:220–225° C.

Analysis for $C_{24}H_{25}N_3O_3$:
Calculated: C,71.44;H,6.25;N,10.41;
Found:C,71.56;H,6.23;N,10.36%.

EXAMPLE 10

Trans-2-butyl-5-(4-methoxyphenyl)-5,6,11,11a-tetrahydro-1H-imidazo [1',5':1,6]pyrido[3,4-b] indole-1,3(2H)-dione The same method as employed in the preparation of Example 1 but starting from the Intermediate 4 and butyl isocyanate gave after recrystallisation from ethanol/water, the title compound as white crystals m.p.:173–174° C.

Analysis for $C_{24}H_{25}N_3O_3$:
Calculated: C,71.44;H,6.25;N,10.41;
Found:C,71.53;H,6.20;N,10.28%.

EXAMPLE 11

Cis-2-butyl-9-fluoro-5-(4-methoxyphenyl)-5,6,11, 11a-tetrahydro-1H-imidazo [1',5':1,6] pyrido [3,4-b] indole-1,3(2H)-dione The same method as employed in the preparation of Example 1 but starting from Intermediate 8 and butyl isocyanate gave after recrystallisation from methanol, the title compound as white crystals m.p.:125–130° C.

Analysis for $C_{24}H_{24}FN_3O_3$ (0.3$H_2O$)
Calculated: C,67.53;H,5.81;N,9.84;
Found:C,67.19;H,5.74,N,9.85%.

EXAMPLE 12

Trans-2-butyl-9-fluoro-5-(4-methoxyphenyl)-5,6,11, 11a-tetrahydro-1H-imidazo [1',5':1,6] pyrido[3,4-b] indole-1,3(2H)-dione The same method as employed in the preparation of Example 1 but starting from the Intermediate 9 and butyl isocyanate gave after recrystallisation from diisopropyl ether/pentane, the title compound as white crystals m.p.:187–189° C.

Analysis for $C_{24}H_{24}FN_3O_3$:
Calculated: C,68.39;H,5.74;N,9.97;
Found:C,68.61;H,5.71;N,10.04%.

EXAMPLE 13

Trans-2-butyl-5-(3,4-methylenedioxyphenyl)-5,6,11, 11a-tetrahydro-1H-imidazo [1',5':1,6]pyrido[3,4-b] indole-1,3(2H)-dione The same method as employed in the preparation of Example 1 but starting from Intermediate 2 and butyl isocyanate gave after recrystallisation from 2-propanol, the title compound as white crystals m.p.:152° C.

Analysis for $C_{24}H_{23}N_3O_4$:
Calculated: C,69.05;H,5.55;N,10.07;
Found:C,68.93;H,5.49;N,9.99%.

EXAMPLE 14

Cis-2-butyl-5-(3-chlorophenyl)-5,6,11,11a-tetrahydro-1H-imidazo[1',5':1,6]pyrido [3,4-b] indole-1,3(2H)-dione and Trans-2-butyl-5-(3-chlorophenyl)-5,6,11,11a-tetrahydro-1H-imidazo[1',5':1,6]pyrido [3,4-b]indole-1,3(2H)-dione The same method as employed in the preparation of Example 1 but starting from a mixture of cis and trans isomers of Intermediate 27 and butyl isocyanate gave the cis isomer as pale yellow crystals after recrystallisation from diethyl ether/cyclohexane m.p.:215–217° C.

Analysis for $C_{23}H_{22}ClN_3O_2$:
Calculated: C,67.73;H,5.44;Cl,8.69;N,10.30;
Found:C,67.62;H,5.49;Cl,8.59;N,10.03%.

and the trans isomer as white crystals after recrystallisation from ethanol m.p.: 207–209° C.

Analysis for $C_{23}H_{22}ClN_3O_2$:
Calculated: C,67.73;H,5.44;Cl,8.69;N,10.30;
Found:C,67.60;H,5.41 ;Cl,8.77;N,10.20%.

EXAMPLE 15

Cis-2-butyl-5-(4-chlorophenyl)-5,6,11,11a-tetrahydro-1H-imidazo [1',5':1,6]pyrido [3,4-b] indole-1,3(2H)-dione The same method as employed in the preparation of Example 1 but starting from Intermediate 10 and butyl isocyanate gave after recrystallisation from methanol, the title compound as pale yellow crystals m.p.:252° C.

Analysis for $C_{23}H_{22}ClN_3O_2$:
Calculated: C,67.73;H,5.44;Cl,8.69;N,10.30;
Found:C,67.60;H,5.44;Cl,8.55;N,10.30%.

EXAMPLE 16

Trans-2-butyl-5-(4-chlorophenyl)-5,6,11,11a-tetrahydro-1H-imidazo [1',5':1,6]pyrido[3,4-b] indole-1,3(2H)-dione The same method as employed in the preparation of Example 1 but starting from Intermediate 11 and butyl isocyanate gave after recrystallisation from methanol, the title compound as pale yellow crystals m.p.:174° C.

Analysis for $C_{23}H_{22}ClN_3O_2$:
Calculated: C,67.73;H,5.44;Cl,8.69;N,10.30;
Found:C,67.75;H,5.49;Cl,8.75;N,10.46.%

EXAMPLE 17

Trans-2-butyl-5-(4-fluorophenyl)-5,6,11,11a-tetrahydro-1H-imidazo[1',5':1,6]pyrido [3,4-b] indole-1,3(2H)-dione The same method as employed in the preparation of Example 1 but starting from the trans isomer of Intermediate 28 and butyl isocyanate gave after recrystallisation from 2-propanol, the title compound as pale yellow crystals m.p. :242° C.

Analysis for $C_{23}H_{22}FN_3O_2$:
Calculated: C,70.57;H,5.66;F,4.85;N,10.73;
Found:C,70.57;H,5.63;F,4.66;N,10.83%.

EXAMPLE 18

Trans-2-butyl-5-(4-hydroxyphenyl)-5,6,11,11a-tetrahydro-1H-imidazo[1',5':1,6]pyrido [3,4-b] indole-1,3(2H)-dione The same method as employed in the preparation of Example 1 but starting from Intermediate 29 and butyl isocyanate gave after recrystallisation from 2-propanol/water, the title compound as white crystals m.p.:259° C.

Analysis for $C_{23}H_{23}N_3O_3$:
Calculated: C,70.93;H,5.95;N,10.79;
Found:C,70.41 ;H,6.04;N, 10.63%.

EXAMPLE 19

Cis-2-butyl-5-(4-trifluoromethylphenyl)-5,6,11,11a-tetrahydro-1H-imidazo [1',5':1,6]pyrido[3,4-b] indole-1,3(2H)-dione The same method as employed in the preparation of Example 1 but starting from Intermediate 12 and butyl isocyanate gave after recrystallisation from methanol/water, the title compound as pale yellow crystals m.p.:232° C.

Analysis for $C_{24}H_{22}F_3N_3O_2$:
Calculated: C,65.30;H,5.02;F,12.91;N,9.52;
Found:C,65.29;H,5.05;F,12.56;N,9.37%.

EXAMPLE 20

Cis-2-butyl-5-(4-cyanophenyl)-5,6,11,11a-tetrahydro-1H-imidazo[1',5':1,6] pyrido [3,4-b] indole-1,3(2H)-dione The same method as used in the preparation of Example 1 but starting from Intermediate 14 and butyl isocyanate gave after recrystallisation from 2-propanol, the title compound as white crystals m.p.:260° C.

Analysis for $C_{24}H_{22}N_4O_2$:
Calculated: C,72.34;H,5.57;N,14.06;
Found:C,72.30;H,5.59;N,14.08%.

EXAMPLE 21

Trans-2-butyl-5-(4-cyanophenyl)-5,6,11,11a-tetrahydro-1H-imidazo[1',5':1,6]pyrido[3,4-b]indole-1,3(2H)-dione The same method as employed in the preparation of Example 1 but starting from Intermediate 15 and butyl isocyanate gave after recrystallisation from diethyl ether/cyclohexane, the title compound as white crystals m.p.:158° C.

Analysis for $C_{24}H_{22}N_4O_2$:
Calculated: C,72.34;H,5.57;N,14.06;
Found:C,72.40;H,5.56;N,13.95%.

EXAMPLE 22

Cis-2-butyl-5-(4-nitrophenyl)-5,6,11,11a-tetrahydro-1H-imidazo[1',5':1,6]pyrido [3,4-b]indole-1,3(2H)-dione and Trans-2-butyl-5-(4-nitrophenyl)-5,6,11,11a-tetrahydro-1H-imidazo[1',5':1,6]pyrido[3,4-b] indole-1,3(2H)-dione The same method as employed in the preparation of Example 1 but starting from a mixture of Intermediates 16 and 17 and butyl isocyanate gave the cis isomer as yellow crystals after recrystallisation from methanol m.p.:236° C.

Analysis for $C_{23}H_{22}N_4O_4$:
Calculated: C,66.02;H,5.30;N,13.39;
Found:C,65.82;H,5.36;N,13.25%.

and the trans isomer as yellow crystals after recrystallisation from 2-propanol m.p.:206° C.

Analysis for $C_{23}H_{22}N_4O_4$:
Calculated: C,66.02;H,5.30;N,13.39;
Found:C,66.12;H,5.38;N,13.28%.

EXAMPLE 23

Cis-2-butyl-5-(3-pyridyl)-5,6,11,11a-tetrahydro-1H-imidazo[1',5':1,6]pyrido [3,4-b]indole-1,3(2H)-dione The same method as employed in the preparation of Example 1 but starting from Intermediate 18 and butyl isocyanate gave after recrystallisation from 2-propanol, the title compound as white crystals m.p.:257–263° C.

Analysis for $C_{22}H_{22}N_4O_2$:
Calculated: C,70.57;H,5.92;N,14.96;
Found:C,70.38;H,6.07;N,14.88%.

EXAMPLE 24

Cis-2-butyl-5-(3-thienyl)-5,6,11,11a-tetrahydro-1H-imidazo[1',5':1,6]pyrido [3,4-b]indole-1,3(2H)-dione and Trans-2-butyl-5-(3-thienyl)-5,6,11,11a-tetrahydro-1H-imidazo[1',5':1,6]pyrido[3,4-b]indole-1,3(2H)-dione The same method as employed in the preparation of Example 1 but starting from a mixture of Intermediates 20 and 21 and butyl isocyanate gave the cis isomer as white crystals after recrystallisation from 2-propanol m.p.:219–221° C.

Analysis for $C_{21}H_{21}N_3O_2S$:
Calculated: C,66.47;H,5.58;N,11.07;S,8.45;
Found:C,66.13;H,5.68;N,11.00;S,8.27%.

and the trans isomer as white crystals after recrystallisation from ethyl acetate m.p.:240–242° C.

Analysis for $C_{21}H_{21}N_3O_2S$:
Calculated: C,66.47;H,5.58;N,11.07;S,8.45;
Found:C,66.68;H,5.69;N,11.05;S,8.56%.

EXAMPLE 25

Cis-2-butyl-5-(3-furyl)-5,6,11,11a-tetrahydro-1H-imidazo[1',5':1,6]pyrido [3,4-b]indole-1,3(2H)-dione and Trans-2-butyl-5-(3-furyl)-5,6,11,11a-tetrahydro-1H-imidazo[1',5':1,6] pyrido[3,4-b]indole-1,3(2H)-dione The same method but starting from a mixture of cis and trans isomers Intermediate 22 and butyl isocyanate gave the cis isomer as white crystals after recrystallisation from toluene m.p.:155–160° C.

Analysis for $C_{21}H_{21}N_3O_3$:
Calculated: C,69.41;H,5.82;N, 11.56;
Found:C,69.44;H,5.86;N,11.52%.

and the trans isomer as pale yellow crystals after recrystallisation from ethanol m.p.:215–219° C.

Analysis for $C_2H_{21}N_3O_3$:
Calculated: C,69.41;H,5.82;N,11.56;
Found:C,69.43;H,5.73;N,11.46%.

EXAMPLE 26

Cis-2-cyclohexyl-5-(4-methoxyphenyl)-5,6,11,11a-tetrahydro-1H-imidazo [1',5':1,6] pyrido[3,4-b]indole-1,3(2H)-dione and Trans-2-cyclohexyl-5-(4-methoxyphenyl)-5,6,11,11a-tetrahydro-1H-imidazo[1',5':1,6] pyrido[3,4-b]indole-1,3(2H)-dione The same method as employed in the preparation of Example 1 but starting from a mixture of Intermediates 3 and 4 and cyclohexyl isocyanate gave the cis isomer as white crystals after recrystallisation from ethanol m.p.:250–260° C.

Analysis for $C_{26}H_{27}N_3O_3$:
Calculated: C,72.71;H,6.34;N,9.78;
Found:C,72.73;H,6.39;N,9.63%.

and the trans isomer as white crystals after recrystallisation from 2-propanol m.p.:265–269° C.

Analysis for $C_{26}H_{27}N_3O_3$:
Calculated: C,72.71;H,6.34;N,9.78;
Found:C,72.82;H,6.38;N,9.69%.

EXAMPLE 27

Cis-2-cyclohexyl-9-fluoro-5-(4-methoxyphenyl)-5,6,11,11a-tetrahydro-1H-imidazo [1',5':1,6] pyrido[3,4-b]indole-1,3(2H)-dione The same method as employed in the preparation of Example 1 but starting from Intermediate 8 and cyclohexyl isocyanate gave after recrystallisation from methanol, the title compound as white crystals m.p.:275–278° C.

Analysis for $C_{26}H_{26}FN_3O_3$:
Calculated: C,69.78;H,5.86;N,9.39;
Found:C,69.75;H,5.85;N,8.96%.

EXAMPLE 28

Trans-2-cyclohexyl-9-fluoro-5-(4-methoxyphenyl)-5,6,11,11a-tetrahydro-1H-imidazo [1',5':1,6] pyrido [3,4-b]indole-1,3(2H)-dione The same method as employed in the preparation of Example 1 but starting from Intermediate 9 and cyclohexyl isocyanate gave after recrystallisation from ethanol, the title compound as white crystals m.p.:265–267° C.

Analysis for $C_{26}H_{26}FN_3O_3$:
Calculated: C,69.78;H,5.86;N,9.39;
Found:C,69.71;H,5.91;N,9.37%.

EXAMPLE 29

Trans-2-benzyl-5-phenyl-5,6,11,11a-tetrahydro-1H-imidazo[1',5':1,6]pyrido [3,4-b]indole-1,3(2H)-dione The same method as employed in the preparation of Example 1 but starting from trans methyl 1,2,3,4-tetrahydro-1-phenyl-9H-pyrido[3,4-b]indole-3-carboxylate[1] and benzyl isocyanate gave after recrystallisation from diethyl ether, the title compound as white crystals m.p.:200–202° C.

Analysis for $C_{26}H_{21}N_3O_2$:
Calculated: C,76.64;H,5.19;N,10.31;
Found:C,76.75;H,5.18;N,10.23%.

1. Cook J., Sandrin J. and Soerens D., Heterocycles, 4, no. 7, 1249–1255 (1976).

EXAMPLE 30

Cis-2-benzyl-5-(4-methoxyphenyl)-5,6,11,11a-tetrahydro-1H-imidazo[1',5':1,6]pyrido [3,4-b]indole-1,3(2H)-dione The same method as employed in the preparation of Example 1 but starting from Intermediate 3 and benzyl isocyanate gave after recrystallisation from ethanol, the title compound as pale yellow crystals m.p.:240–243° C.

Analysis for $C_{27}H_{23}N_3O_3$:
Calculated: C,74.13;H,5.30;N,9.60;
Found:C,74.13;H,5.31 ;N,9.58%.

EXAMPLE 31

Trans-2-benzyl-5-(4-methoxyphenyl)-5,6,11,11a-tetrahydro-1H-imidazo[1',5':1,6]pyrido [3,4-b]indole-1,3(2H)-dione The same method as employed in the preparation of Example 1 but starting from Intermediate 4 and benzyl isocyanate gave after recrystallisation from 2-propanol, the title compound as white crystals m.p.:208–212° C.

Analysis for $C_{27}H_{23}N_3O_3$:
Calculated: C,74.13;H,5.30;N,9.60;
Found:C,74.25;H,5.47;N,9.49%.

EXAMPLE 32

(5R,11aR)-2-benzyl-5-(3,4-methylenedioxyphenyl)-5,6,11,11a-tetrahydro-1H-imidazo [1',5':1,6]pyrido [3,4-b]indole-1,3(2H)-dione The same method as employed in the preparation of Example 1 but starting from Intermediate 23 and benzyl isocyanate, gave after recrystallisation toluene, the title compound as white crystals m.p.:145° C.

Analysis for $C_{27}H_{21}N_3O_4$:
Calculated: C,71.83;H,4.69;N,9.31;
Found:C,71.47;H,4.74;N,9.28%.

EXAMPLE 33

Trans-2-benzyl-5-(4-hydroxyphenyl)-5,6,11,11a-tetrahydro-1H-imidazo [1',5':1,6]pyrido [3,4-b]indole-1,3(2H)-dione The same method as employed in the preparation of Example 1 but starting from Intermediate 29 and benzyl isocyanate gave after recrystallisation from methanol, the title compound as white crystals m.p.:268–272° C.

Analysis for $C_{26}H_{21}N_3O_3$:
Calculated: C,73.74;H,5.00;N,9.92;
Found:C,73.63;H,5.09;N,10.02%.

EXAMPLE 34

Trans-2-(2-chloroethyl)-5-(4-methoxyphenyl)-5,6,11,11a-tetrahydro-1H-imidazo [1',5':1,6] pyrido[3,4-b]indole-1,3(2H)-dione The same method as employed in the preparation of Example 1 but starting from Intermediate 4 and 2-chloroethyl isocyanate, gave after recrystallisation from diethyl ether/hexane, the title compound as white crystals m.p.:218–219° C.

Analysis for $C_{22}H_{20}ClN_3O_3$:
Calculated: C,64.47;H,4.92;Cl,8.65;N,10.25;
Found:C,64.44;H,4.98;Cl,8.81;N,10.20%.

EXAMPLE 35

Cis-2-benzyl-5-cyclohexyl-5,6,11,11a-tetrahydro-1H-imidazo[1',5':1,6]pyrido[3,4-b]indole-1,3(2H)-dione The same method as employed in the preparation of Example 1 but starting from cis methyl 1,2,3,4-tetrahydro-1-cyclohexyl-9H-pyrido[3,4-b]indole-3-carboxylate[1] and benzyl isocyanate gave after recrystallisation from methanol, the title compound as white crystals m.p.:170–173° C.

Analysis for C26H27N3O2:
Calculated: C,75.52;H,6.58;N,10.16;
Found:C,75.63;H,6.48;N,9.75%.

1. Cook J., Sandrin J. and Soerens D., Heterocycles, 4, no 7, 1249–1255 (1976).

EXAMPLE 36

Trans-2-benzyl-5-cyclohexyl-5,6,11,11a-tetrahydro-1H-imidazo[1',5':1,6]pyrido[3,4-b]indole-1,3(2H)-dione The same method as employed in the preparation of Example 1 but starting from trans methyl 1,2,3,4-tetrahydro-1-cyclohexyl-9H-pyrido[3,4-b]indole-3-carboxylate[1] and benzyl isocyanate gave after recrystallisation from methanol, the title compound as white crystals m.p.:130–135° C.

Analysis for C26H27N3O2:
Calculated: C,75.52;H,6.58;N,10.16;
Found:C,75.74;H,6.67;N,9.94%.

1 . Cook J., Sandrin J. and Soerens D., Heterocycles, 4, no 7, 1249–1255 (1976).

EXAMPLE 37

Trans-2-butyl-5-phenyl-5,6,11,11a-tetrahydro-1H-imidazo[1',5':1,6]pyrido[3,4-b]indole-1,3(2H)-dione The same method as employed in the preparation of Example 1 but starting from trans methyl 1,2,3,4-tetrahydro-1-phenyl-9H-pyrido[3,4-b]indole-3-carboxylate and butyl isocyanate gave after recrystallisation from 2-propanol, the title compound as white crystals m.p.:240–243° C.

Analysis for C23H23N3O2:
Calculated: C,73.97;H,6.21;N,11.25;
Found:C,73.95;H,6.32;N,11.28%.

EXAMPLE 38

Trans-2-cyclohexyl-5-phenyl-5,6,11,11a-tetrahydro-1H-imidazo[1',5':1,6] pyrido [3,4-b]indole-1,3(2H)-dione The same method as employed in the preparation of Example 1 but starting from trans methyl 1,2,3,4-tetrahydro-1-phenyl-9H-pyrido[3,4-b]indole-3-carboxylate and cyclohexyl isocyanate gave after recrystallisation from methanol, the title compound as white crystals m.p.:248–250° C.

Analysis for C25H25N3O2:
Calculated: C,75.16;H,6.31 ;N,10.52;
Found:C,75.23;H,6.33;N,10.60%.

EXAMPLE 39

Cis-2-cyclohexyl-5-phenyl-5,6,11,11a-tetrahydro-1H-imidazo[1',5':1,6] pyrido [3,4-b]indole-1,3(2H)-dione The same method as employed in the preparation of Example 1 but starting from cis methyl 1,2,3,4-tetrahydro-1-phenyl-9H-pyrido[3,4-b]indole-3-carboxylate and cyclohexyl isocyanate gave after recrystallisation from methanol, the title compound as white crystals m.p.:267–270° C.

Analysis for C25H25N3O2:
Calculated: C,75.16;H,6.31;N,10.52;
Found:C,75.20;H,6.33;N,10.52%.

EXAMPLE 40

Trans-2-ethoxycarbonylmethyl-5-(4-methoxyphenyl)-5,6,11,11a-tetrahydro-1H-imidazo [1',5':1,6] pyrido [3,4-b]indole-1,3(2H)-dione The same method as employed in the preparation of Example 1 but starting from Intermediate 4 and ethyl isocyanatoacetate gave after recrystallisation from ethanol, the title compound as white crystals m.p.:165–167° C.

Analysis for C24H23N3O5:
Calculated: C,66.50;H,5.35;N,9.69;
Found:C,66.66;H,5.32;N,9.66%.

EXAMPLE 41

Trans-5-(4-methoxyphenyl)-2-[2-(2-pyridyl)-ethyl]-5,6,11,11a-tetrahydro-1H-imidazo [1',5':1,6]pyrido [3,4-b]indole-1,3(2H)-dione To a stirred solution of carbonyl diimidazole (0.28 g, 1.72 mmol) in dry tetrahydrofuran (5 mL), was added dropwise a solution of 2-(2-aminoethyl) pyridine (0.205 g, 1.68 mmol) in tetrahydrofuran (3 mL) and the solution was stirred at room temperature for 0.5 hour. Then, a solution of Intermediate 4 (0.5 g, 1.43 mmol) in dry tetrahydrofuran (7 mL) was added and the resulting solution was refluxed for 20 hours. The solvent was removed under reduced pressure and the residue was dissolved in dichloromethane (50 mL). The solution was washed three times with water (3×20 mL), dried over Na2SO4 and concentrated. The residue was then purified by flash chromatography eluting with dichloromethane/methanol : 99/1 and recrystallised from ethanol/water to give the title compound (0.35 g) as white crystals m.p.:140–143° C.

Analysis for C27H24N4O3:
Calculated: C,71.67;H,5.35;N,12.38;
Found:C,71.87;H,5.41 ;N,12.28%.

EXAMPLE 42

Trans-2-cyclopropyl-5-phenyl-5,6,11,11a-tetrahydro-1H-imidazo[1',5':1,6]pyrido[3,4-b]indole-1,3(2H)-dione The same method as employed in the preparation of Example 41 but starting from trans methyl 1,2,3,4-tetrahydro-1-phenyl-9H-pyrido[3,4-b]indole-3-carboxylate and cyclopropylamine gave after recrystallisation from ethanol, the title compound as white crystals m.p.:250–255° C.

Analysis for C22H19N3O2:
Calculated: C,73.93;H,5.36;N,11.76;
Found:C,73.84;H,5.45;N,11.63%.

EXAMPLE 43

Trans -2-phenethyl-5-phenyl-5,6,11,11a-tetrahydro-1H-imidazo[1',5':1,6]pyrido[3,4-b]indole-1,3(2H)-dione The same method as employed in the preparation of Example 41 but starting from trans methyl 1,2,3,4-tetrahydro-1-phenyl-9H-pyrido[3,4-b]indole-3-carboxylate and phenethylamine gave after recrystallisation from diethyl ether, the title compound as white crystals m.p.:240–242° C.

Analysis for C27H23N3O2:
Calculated: C,76.94;H,5.50;N,9.97;
Found:C,77.20;H,5.65;N,10.05%.

EXAMPLE 44

Trans-5-phenyl-2-(2-pyridylmethyl)-5,6,11,11a-tetrahydro-1H-imidazo [1',5':1,6]pyrido[3,4-b]indole-1,3(2H)-dione The same method as employed in the preparation of Example 41 but starting from trans methyl 1,2,3,4-tetrahydro-1-phenyl-9H-pyrido[3,4-b]indole-3-carboxylate and 2-(aminomethyl) pyridine, gave after recrystallisation from methanol, the title compound as white crystals m.p.:165–175° C.

Analysis for C25H20N4O2:
Calculated: C,73.51;H,4.94;N,13.72;
Found:C,73.46;H5.29;N,13.84%.

EXAMPLE 45

Trans-5-phenyl-2-(4-pyridylmethyl)-5,6,11,11a-tetrahydro-1H-imidazo [1',5':1,6]pyrido[3,4-b]indole-1,3(2H)-dione The same method as employed in the preparation of Example 41 but starting from trans methyl 1,2,3,4-tetrahydro-1-phenyl-9H-pyrido[3,4-b]indole-3-carboxylate and 4-(aminomethyl) pyridine, gave after recrystallisation from methanol, the title compound as white crystals m.p.:247–249° C.

Analysis for C25H20N4O2:
Calculated: C,73.51;H,4.94;N,13.72;
Found:C,73.41;H,4.98;N,13.62%.

EXAMPLE 46

Trans-5-(4-methoxyphenyl)-2-(3-pyridylmethyl)-5,6,11,11a-tetrahydro-1H-imidazo [1',5':1,6]pyrido[3,4-b]indole-1,3(2H)-dione The same method as employed in the preparation of Example 41 but starting from Intermediate 4 and 3-(aminomethyl) pyridine, gave after recrystallisation from ethanol, the title compound as white crystals m.p.:160–165° C.

Analysis for C26H22N4O3:
Calculated: C,71.22;H,5.06;N,12.78;
Found:C,71.12;H,5.15;N,12.59%.

EXAMPLE 47

Trans-2-(2-dimethylamino-ethyl)-5-(4-methoxyphenyl)-5,6,11,11a-tetrahydro-1H-imidazo [1',5':1,6]pyrido [3,4-b]indole-1,3(2H)-dione The same method as employed in the preparation of Example 41 but starting from Intermediate 4 and N,N- dimethyl-ethane-1,2-diamine, gave after recrystallisation from ethanol/water, the title compound as pale yellow crystals m.p.:120–124° C.

Analysis for C24H26N4O3:
Calculated: C,68.88;H,6.26;N,13.39;
Found:C,68.91;H,6.43.N,13.23%.

EXAMPLE 48

Trans-2-(3-dimethylamino-propyl)-5-(4-methoxyphenyl)-5,6,11,11a-tetrahydro-1H-imidazo [1',5':1,6] pyrido [3,4-b]indole-1,3(2H)-dione The same method as employed in the preparation of Example 41 but starting from Intermediate 4 and N,N-dimethyl-propane-1,3-diamine, gave after recrystallisation from ethyl acetate/hexane, the title compound as white crystals m.p.:159–161° C.

Analysis for C25H28N4O3:
Calculated: C,69.42;H,6.53;N,12.95;
Found:C,68.89;H,6.60;N,12.91%.

EXAMPLE 49

Trans-2-(2-morpholin-4-yl-ethyl)-5-phenyl-5,6,11,11a-tetrahydro-1H-imidazo [1',5':1,6] pyrido [3,4-b]indole-1,3(2H)-dione The same method as employed in the preparation of Example 41 but starting from trans methyl 1,2,3,4-tetrahydro-1-phenyl-9H-pyrido[3,4-b]indole-3-carboxylate and 2-morpholin-4-yl-ethylamine, gave after recrystallisation from ethanol, the title compound as white crystals m.p.:183–185° C.

Analysis for C25H26N4O3:
Calculated: C,69.75;H,6.09;N,13.01;
Found:C,69.68;H,6.17;N,12.80%.

EXAMPLE 50

Trans-5-(4-methoxyphenyl)-2-[3-(4-methyl-piperazin-1-yl)-propyl]- 5,6,11,11-tetrahydro-1H-imidazo [1',5':1,6] pyrido [3,4-b]indole-1,3(2H)-dione The same method as employed in the preparation of Example 41 but starting from Intermediate 4 and 3-(4-methyl-piperazin-1-yl)-propylamine, gave after recrystallisation from ethanol/water, the title compound as white crystals m.p.: 164–168° C.

Analysis for C28H33N5O3 (0.5 H2O):
Calculated: C,67.72;H,6.9;N,14.1;
Found:C,67.85;H,6.75;N,14.13%.

EXAMPLE 51

Trans-5-(4-methoxyphenyl)-2-(2-pyrrolidin-1-yl-ethyl)-5,6,11,11a-tetrahydro-1H-imidazo [1',5':1,6] pyrido [3,4-b]indole-1,3(2H)-dione The same method as employed in the preparation of Example 41 but starting from Intermediate 4 and 2-pyrrolidin-1-yl-ethylamine, gave after recrystallisation from ethanol/water, the title compound as white crystals m.p.:126–130° C.

Analysis for C26H28N4O3:
Calculated: C,70.25;H,6.35;N,12.00;
Found:C,69.99;H,6.35;N,12.50%.

EXAMPLE 52

Trans-5-(4-methoxyphenyl)-2-[2-(1-methyl-pyrrolidin-2-yl)-ethyl]-5,6,11,11a-tetrahydro-1H-imidazo [1',5':1,6] pyrido [3,4-b]indole-1,3(2H)-dione The same method as employed in the preparation of Example 41 but starting from Intermediate 4 and 2-(1-methyl-pyrrolidin-2-yl)-ethylamine, gave after recrystallisation from methanol, the title compound as white crystals m.p.:170–180° C.

Analysis for C27H30N4O3:
Calculated: C,70.72;H,6.59;N,12.22;
Found:C,70.86;H,6.62;N,12.41%.

EXAMPLE 53

Trans-5-(4-methoxyphenyl)-5,6,11,11a-tetrahydro-1H-imidazo[1',5':1,6] pyrido [3,4-b]indole-1,3 (2H)-dione A mixture of Intermediate 4 (0.5 g, 1.48 mmol) and urea (0.1 g) was heated at 220° C. for a few minutes. The reaction was then cooled to room temperature and the solid suspended in methanol, filtered then recrystallised from hot methanol to give the title compound as off-white crystals m.p.:295–305° C.

Analysis for C20H17N3O3:
Calculated: C,69.15;H,4.93;N,12.10;
Found:C,68.87;H,4.95;N,12.00%.

EXAMPLE 54

Cis-5-(4-methoxyphenyl)-5,6,11,11a-tetrahydro-1H-imidazo[1',5':1,6] pyrido [3,4-b]indole-1,3 (2H)-dione The same method as employed in the preparation of Example 53 but starting from Intermediate 3 and urea, gave after recrystallisation from methanol, the title compound as pale yellow crystals m.p.:300–310° C.

Analysis for C20H17N3O3:
Calculated: C,69.15;H,4.93;N,12.10;
Found:C,68.90;H,4.91;N,11.98%.

TABLETS FOR ORAL ADMINISTRATION

A. Direct Compression

| 1. | mg/tablet |
|---|---|
| Active ingredient | 50.0 |
| Crospovidone USNF | 8.0 |
| Magnesium Stearate Ph Eur | 1.0 |
| Anhydrous Lactose | 141.0 |

The active ingredient was sieved and blended with the excipients. The resultant mix was compressed into tablets.

| 2. | mg/tablet |
|---|---|
| Active ingredient | 50.0 |
| Colloidal Silicon Dioxide | 0.5 |

-continued

| 2. | mg/tablet |
|---|---|
| Crospovidone | 8.0 |
| Sodium Lauryl Sulphate | 1.0 |
| Magnesium Stearate Ph Eur | 1.0 |
| Microcrystalline Cellulose USNF | 139.5 |

The active ingredient was sieved and blended with the excipients. The resultant mix was compressed into tablets.

B. Wet Granulation

| 1. | mg/tablet |
|---|---|
| Active ingredient | 50.0 |
| Polyvinyl pyrollidone | 150.0 |
| Polyethylene glycol | 50.0 |
| Polysorbate 80 | 10.0 |
| Magnesium Stearate Ph Eur | 2.5 |
| Croscarmellose Sodium | 25.0 |
| Colloidal Silicon Dioxide | 2.5 |
| Microcrystalline Cellulose USNF | 210.0 |

The polyvinyl pyrollidone, polyethylene glycol and polysorbate 80 were dissolved in water. The resultant solution was used to granulate the active ingredient. After drying the granules were screened, then extruded at elevated temperatures and pressures. The extrudate was milled and/or screened then was blended with the microcrystalline cellulose, croscarmellose sodium, colloidal silicon dioxide and magnesium stearate. The resultant mix was compressed into tablets.

| 2. | mg/tablet |
|---|---|
| Active ingredient | 50.0 |
| Polysorbate 80 | 3.0 |
| Lactose Ph Eur | 178.0 |
| Starch BP | 45.0 |
| Pregelatinised Maize Starch BP | 22.5 |
| Magnesium Stearate BP | 1.5 |

The active ingredient was sieved and blended with the lactose, starch and pregelatinised maize starch. The polysorbate 80 was dissolved in purified water. Suitable volumes of the polysorbate 80 solution were added and the powders were granulated. After drying, the granules were screened and blended with the magnesium stearate. The granules were then compressed into tablets.

Tablets of other strengths may be prepared by altering the ratio of active ingredient to the other excipients.

FILM COATED TABLETS

The aforementioned tablet formulations were film coated.

| Coating Suspension | % w/w |
|---|---|
| Opadry white† | 13.2 |
| Purified water Ph Eur | to100.0* |

The water did not appear in the final product. The maximum theoretical weight of solids applied during coating was 20 mg/tablet.

†Opadry white is a proprietary material obtainable from Colorcon Limited, UK which contains hydroxypropyl methylcellulose, titanium dioxide and triacetin.

The tablets were film coated using the coating suspension in conventional film coating equipment.

Capsules

| 1. | mg/capsule |
|---|---|
| Active ingredient | 50.0 |
| Lactose | 148.5 |
| Polyvinyl pyrollidone | 100.0 |
| Magnesium Stearate | 1.5 |

The active ingredient was sieved and blended with the excipients. The mix was filled into size No. 1 hard gelatin capsules using suitable equipment.

| 2. | mg/capsule |
|---|---|
| Active ingredient | 50.0 |
| Microcrystalline Cellulose | 233.5 |
| Sodium Lauryl Sulphate | 3.0 |
| Crospovidone | 12.0 |
| Magnesium Stearate | 1.5 |

The active ingredient was sieved and blended with the excipients. The mix was filled into size No. 1 hard gelatin capsules using suitable equipment.

Other doses may be prepared by altering the ratio of active ingredient to excipient, the fill weight and if necessary changing the capsule size.

| 3. | mg/capsule |
|---|---|
| Active ingredient | 50.0 |
| Labrafil M1944CS | to1.0 ml |

The active ingredient was sieved and blended with the Labrafil. The suspension was filled into soft gelatin capsules using appropriate equipment.

Inhibitory effect on cGMP-PDE cGMP-PDE activity of compounds of the present invention was measured using a one-step assay adapted from Wells at al. (Wells, J. N., Baird, C. E., Wu, Y. J. and Hardman, J. G., Biochim. Biophys. Acta 384, 430 (1975)). The reaction medium contained 50 mM Tris-HCl, pH 7.5, 5 mM Mg-acetate, 250µg/ml 5'-Nucleotidase, 1 mM EGTA and 0.15µM 8-[$H^3$]-cGMP. The enzyme used was a human recombinant PDE V (ICOS, Seattle USA).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves using typically concentrations ranging from 10 nM to 10µM. Tests against other PDE enzymes using standard methodology also showed that compounds of the invention are highly selective for the CGMP specific PDE enzyme.

cGMP level measurements Rat aortic smooth muscle cells (RSMC) prepared according to Chamley et al. in Cell Tissue Res. 177, 503–522 (1977) were used between the 10th and 25th passage at confluence in 24-well culture dishes. Culture media was aspirated and replaced with PBS (0.5 ml) containing the compound tested at the appropriate concentration. After 30 minutes at 37° C., particulates guanylate cyclase was stimulated by addition of ANF (100 nM) for 10 minutes. At the end of incubation, the medium was withdrawn and two extractions were performed by addition of 65% ethanol (0.25 ml). The two ethanolic extracts were pooled and evaporated until dryness, using a Speed-vac system. c-GMP was measured after acetylation by scintillation proximity immunoassay (AMERSHAM). The $EC_{50}$ values are expressed as the dose giving half of the stimulation at saturating concentrations

BIOLOGICAL DATA

The compounds according to the present invention were typically found to exhibit an $IC_{50}$ value of less than 500 nM and an $EC_{50}$ value of less than 5 $\mu$M. In vitro test data for representative compounds of the invention is given in the following table:

TABLE 1

In vitro results

| Example No. | $IC_{50}$ nM | $EC_{50}$ $\mu$M |
|---|---|---|
| 10 | 4 | <1 |
| 26 (cis isomer) | 7 | 0.3 |
| 1 (cis isomer) | <10 | 0.3 |
| 32 | <10 | 0.2 |

The hypotensive effects of compounds according to the invention as identified in Table 2 were studied in conscious spontaneously hypertensive rats (SHRs). The compounds were administered orally at a dose of 5 or 10 mg/kg in a mixture of 5% DMF and 95% olive oil, or i.v. at a dose of 10 mg/kg in a mixture of 40% dimethylformamide, 25% tetraglycol, and 25% glucose serum. Blood pressure was measured from a catheter inserted in the carotid artery and recorded for 5 hours after administration. The results are expressed as Area Under the Curve (AUC from 0 to 5 hours, mmHg.hour) of the fall in blood pressure over time.

TABLE 2

In vitro results

| Example No. | AUC (mmHg.h) |
|---|---|
| 10 | 147 (dosed at 10 mg/kg i.v.) |
| 26 (cis isomer) | 117 (dosed at 10 mg/kg i.v.) |
| 1 (cis isomer) | 104 (dosed at 5 mg/kg p.o.) |
| 32 | 65 (dosed at 5 mg/kg p.o.) |

We claim:
1. A compound of formula (I)

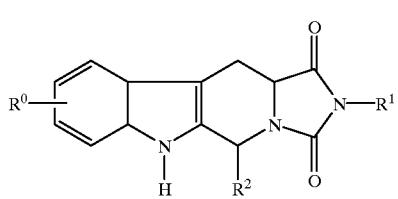

(I)

and salts and solvates thereof, in which:
 $R^0$ represents hydrogen, halogen or $C_{1-6}$alkyl;
 $R^1$ is selected from the group consisting of:
  (a) hydrogen;
  (b) $C_{1-6}$alkyl optionally substituted by one or more substituents selected from phenyl, halogen, —$CO_2R^a$ and —$NR^aR^b$;
  (c) $C_{3-6}$cycloalkyl;
  (d) phenyl; and
  (e) a 5- or 6-membered heterocyclic ring containing at least one heteroatom selected from oxygen, nitrogen and sulphur, and being optionally substituted by one or more $C_{1-6}$alkyl, and optionally linked to the nitrogen atom to which $R^1$ is attached via $C_{1-6}$alkyl;
 $R^2$ is selected from the group consisting of:
  (f) $C_{3-6}$cycloalkyl;
  (g) a 5- or 6-membered heterocyclic ring containing at least one heteroatom selected from oxygen, nitrogen and sulphur; and
  (h) a bicyclic ring

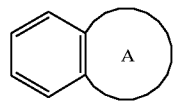

attached to the rest of the molecule via one of the benzene ring carbon atoms and A is a 5- or 6-membered heterocyclic ring as defined in point (g); and
 $R^a$ and $R^b$ independently represent hydrogen or $C_{1-6}$alkyl.
2. A compound according to claim 1 wherein $R^0$ is selected from hydrogen, methyl, bromine and fluorine.
3. A compound according to claim 1 wherein $R^1$ is selected from methyl, ethyl optionally substituted by one or more chlorine atoms, butyl, cyclohexyl and benzyl.
4. A compound according to claim 1 wherein $R^1$ is selected from hydrogen, cycloalkyl, $C_{1-6}$alkyl substituted by an —$NR^aR^b$ substituent, phenyl optionally linked to the nitrogen atom to which $R^1$ is attached via a $C_{1-6}$alkyl chain, and $C_{1-6}$alkyl, substituted by —$CO_2R^a$.
5. A compound according to claim 1 wherein $R^1$ is selected from pyridyl, morpholinyl, piperazinyl, pyrrolidinyl and piperidinyl, such rings being linked to the nitrogen atom to which $R^1$ is attached via a $C_{1-6}$alkyl chain.
6. A compound according to claim 5 wherein the heterocyclic ring is linked to the nitrogen atom to which $R^1$ is attached via a $C_{1-4}$alkyl chain.
7. A compound according to any of claims 1 wherein $R^2$ represents

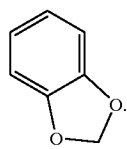

8. A compound according to claim 1 wherein $R^2$ represents thienyl, pyridyl, or furyl.
9. A compound according to claim 1 wherein $R^2$ represents a $C_{3-6}$cycloalkyl group.
10. The method of claim 1 wherein the condition is erectile dysfunction.
11. The method of claim 10 wherein the animal body is human.
12. The method of claim 10 wherein the compound is administered orally.
13. A method of treating conditions where inhibition of cGMP-specific PDE is of therapeutic benefit, in a human or nonhuman animal body, which comprises administering to said body a therapeutically effective amount of a compound having a formula

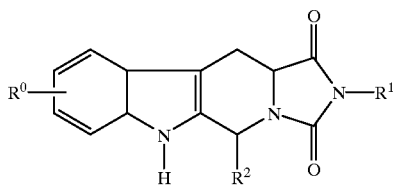

and salts and solvates thereof, in which:
R⁰ represents hydrogen, halogen, or $C_{1-6}$alkyl;
R¹ is selected from the group consisting of:
  (a) hydrogen;
  (b) $C_{1-6}$alkyl optionally substituted by one or more substituents selected from phenyl, halogen, —$CO_2R^a$ and —$NR^aR^b$;
  (c) $C_{3-6}$cycloalkyl;
  (d) phenyl; and
  (e) a 5- or 6-membered heterocyclic ring containing at least one heteroatom selected from oxygen, nitrogen, and sulphur, and being optionally substituted by one or more $C_{1-6}$alkyl, and optionally linked to the nitrogen atom to which R¹ is attached via $C_{1-6}$alkyl;
R² is selected from the group consisting of:
  (f) $C_{3-6}$cycloalkyl;
  (g) a 5- or 6-membered heterocyclic ring containing at least one heteroatom selected from oxygen, nitrogen, and sulphur; and
  (h) a bicyclic ring

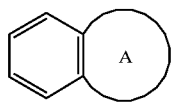

attached to the rest of the molecule via one of the benzene ring carbon atoms and A is a 5- or 6-membered heterocyclic ring as defined in point (h); and $R^a$ and $R^b$ independently represent hydrogen or $C_{1-6}$alkyl.

14. A compound selected from:
Cis-2-benzyl-5-(3,4-methylenedioxyphenyl)-5,6,11,11a-tetrahydro-1H-imidazo [1',5':1,6]pyrido[3,4-b]indole-1,3 (2H) -dione;

Trans-2-benzyl-5-(3,4-methylenedioxyphenyl)-5,6,11,11a-tetrahydro-1H-imidazo [1',5':1,6]pyrido[3,4-b]indole-1,3 (2H) -dione;

Trans-2-ethyl-5-(3,4-methylenedioxyphenyl)-5,6,11,11a-tetrahydro-1H-imidazo [1',5':1,6]pyrido[3,4-b]indole-1,3 (2H) -dione;

Trans-2-ethyl-5-(2-thienyl)-5,6,11,11a-tetrahydro-1H-imidazo [1', 5':1,6]pyrido [3,4-b]indole-1,3(2H)-dione;

Trans-2-butyl-5-(3,4-methylenedioxyphenyl)-5,6,11,11a-tetrahydro-1H-imidazo [1', 5':1,6]pyrido[3,4-b]indole-1,3 (2H) -dione;

Cis-2-butyl-5-(3-pyridyl)-5,6,11,11a-tetrahydro-1H-imidazo [1',5':1,6]pyrido [3,4-b] indole-1,3(2H)-dione;

Cis-2-butyl-5-(3-thienyl)-5,6,11,11a-tetrahydro-1H-imidazo [1',5':1,6]pyrido [3,4-b]indole-1,3(2H)-dione;

Trans-2-butyl-5-(3-thienyl)-5,6,11,11a-tetrahydro-1H-imidazo [1', 5':1,6]pyrido[3,4-b]indole-1,3(2H)-dione;

Cis-2-butyl-5-(3-furyl)-5,6,11,11a-tetrahydro-1H-imidazo [1',5':1,6]pyrido [3,4-b]indole-1,3(2H)-dione;

Trans-2-butyl-5-(3-furyl)-5,6,11,11a-tetrahydro-1H-imidazo [1', 5':1,6]pyrido[3,4-b]indole-1,3(2H)-dione;

(5R,11aR)-2-benzyl-5-(3,4-methylenedioxyphenyl)-5,6,11,11a-tetrahydro-1H-imidazo [1',5':1,6]pyrido[3,4-b]indole-1,3(2H)-dione;

Cis-2-benzyl-5-cyclohexyl-5,6,11,11a-tetrahydro-1H-imidazo [1', 5':1,6]pyrido[3,4-b]indole-1,3(2H)-dione;

Trans-2-benzyl-5-cyclohexyl-5,6,11,11a-tetrahydro-1H-imidazo [1', 5':1,6]pyrido[3,4-b]indole-1,3(2H)-dione;

Trans-5-phenyl-2-(2-pyridylmethyl)-5,6,11,11a-tetrahydro-1H-imidazo [1',5':1,6]pyrido[3,4-b]indole-1,3(2H)-dione;

and pharmaceutically acceptable salts and solvates thereof.

15. (5R,11aR)-2-benzyl-5-(3,4-methylenedioxyphenyl)-5,6,11,11a-tetrahydro-1H-imidazo [1',5':1,6]pyrido[3,4-b]indole-1,3(2H)-dione; Cis-2-benzyl-5-(3,4-methylenedioxyphenyl)-5,6,11,11a-tetrahydro-1H-imidazo [1',5':1,6]pyrido[3,4-b]indole-1,3-(2H)-dione; and pharmaceutically acceptable salts and solvates thereof.

* * * * *

UNITED STATES PATENT AND TRADEMARK OFFICE
CERTIFICATE OF CORRECTION

PATENT NO.: 6,001,847
DATED: December 14, 1999
INVENTOR: Daugan et al.

It is certified that error appears in the above-identified patent and that said Letters Patent is hereby corrected as shown below:

First page, Foreign Application Priority Data, [30], replace "9414473" with "9514473.9".

Second page, Other Publications, first column, under R. Pickard replace "pharamcol" with "pharmacol".

Second page, Other Publications, first column, replace "M. Geimbycz" with "M. Giembycz".

Second page, Other Publications, first column, under R. Pickard replace "pharamcol" with "pharmacol".

First page, U.S. Patent Documents, first column, under Saxena replace "544/343" with "260/268 PC".

First page, Foreign Patent Documents, first column, "1 454 171 10/1975 United Kingdom C07D 471/14" should be deleted.

UNITED STATES PATENT AND TRADEMARK OFFICE
CERTIFICATE OF CORRECTION

Page 2 of 4

PATENT NO.: 6,001,847

DATED: December 14, 1999

INVENTOR: Daugan *et al.*

It is certified that error appears in the above-identified patent and that said Letters Patent is hereby corrected as shown below:

Column 30, line 41, claim 7, replace "any of claims 1" with "claim 1".

Column 30, line 56, claim 10, replace "the method of claim 1" with "the method of claim 13".

Column 4, line 17, a new paragraph should start at "Trans-2-cyclohexyl".

Column 4, line 18, replace "1 1,1 1" with "11,11".

Column 6, line 51, replace "0.2400mg" with "0.2-400mg".

Column 17, line 20, replace "CI" with "Cl".

Column 17, line 26, replace "CI" with "Cl".

Column 17, line 40, replace "CI" with "Cl".

Column 17, line 41, replace "CI" with "Cl".

UNITED STATES PATENT AND TRADEMARK OFFICE
CERTIFICATE OF CORRECTION

PATENT NO.: 6,001,847
DATED: December 14, 1999
INVENTOR: Daugan *et al.*

It is certified that error appears in the above-identified patent and that said Letters Patent is hereby corrected as shown below:

Column 17, line 42, replace "Cl" with "Cl".

Column 17, line 54, replace "Cl" with "Cl".

Column 17, line 55, replace "Cl" with "Cl".

Column 17, line 56, replace "Cl" with "Cl".

Column 20, line 1, replace "$C_2H_{21}N_3O_3$" with "$C_{21}H_{21}N_3O_3$".

Column 22, line 1, replace "Cl" with "Cl".

Column 22, line 1, replace "Cl" with "Cl".

Column 22, line 2, replace "Cl" with "Cl".

Column 22, line 3, replace "Cl" with "Cl".

UNITED STATES PATENT AND TRADEMARK OFFICE
CERTIFICATE OF CORRECTION

PATENT NO.: 6,001,847

DATED: December 14, 1999

INVENTOR: Daugan et al.

It is certified that error appears in the above-identified patent and that said Letters Patent is hereby corrected as shown below:

Column 22, line 35, replace "CI" with "Cl".

Column 27, line 60, insert "*" before "The water".

Column 28, line 42, replace ""Tris-HCI" with "Tris-HCl".

Column 28, line 55, replace "CGMP" with "cGMP".

Column 28, line 56, begin a new paragraph at "Rat aortic".

Signed and Sealed this

Fifteenth Day of May, 2001

*Attest:*

NICHOLAS P. GODICI

*Attesting Officer*     *Acting Director of the United States Patent and Trademark Office*